United States Patent
Sparsø et al.

(10) Patent No.: US 9,045,514 B2
(45) Date of Patent: Jun. 2, 2015

(54) METHODS FOR PRODUCING AMINO-SUBSTITUTED GLYCOLIPID COMPOUNDS

(75) Inventors: Flemming Vang Sparsø, Skanderborg (DK); Karsten Matthias Kragh, Viby J (DK); Lars Wiebe, Grindsted (DK); Rene Mikkelsen, Skanderborg (DK); Anne Katherine Kjærsgaard Laursen, Bryrup (DK)

(73) Assignee: DuPont Nutrition Biosciences ApS, Copenhagen (DK)

( * ) Notice: Subject to any disclaimer, the term of this patent is extended or adjusted under 35 U.S.C. 154(b) by 109 days.

(21) Appl. No.: 13/574,420

(22) PCT Filed: Jan. 20, 2011

(86) PCT No.: PCT/IB2011/050258
§ 371 (c)(1),
(2), (4) Date: Jul. 20, 2012

(87) PCT Pub. No.: WO2011/089561
PCT Pub. Date: Jul. 28, 2011

(65) Prior Publication Data
US 2012/0315373 A1    Dec. 13, 2012

Related U.S. Application Data

(60) Provisional application No. 61/298,760, filed on Jan. 27, 2010.

(30) Foreign Application Priority Data

Jan. 22, 2010   (EP) ..................................... 10151489

(51) Int. Cl.
| | |
|---|---|
| *C07H 15/203* | (2006.01) |
| *C07H 5/06* | (2006.01) |
| *A23K 1/16* | (2006.01) |
| *A23K 1/165* | (2006.01) |
| *A23L 1/03* | (2006.01) |
| *A23L 1/035* | (2006.01) |
| *A23L 1/30* | (2006.01) |
| *A23L 1/305* | (2006.01) |
| *A23L 1/308* | (2006.01) |

(Continued)

(52) U.S. Cl.
CPC ................ *C07H 5/06* (2013.01); *A23K 1/1609* (2013.01); *A23K 1/1653* (2013.01); *A23L 1/031* (2013.01); *A23L 1/035* (2013.01); *A23L 1/30* (2013.01); *A23L 1/305* (2013.01); *A23L 1/308* (2013.01); *A61K 8/60* (2013.01); *A61K 2800/524* (2013.01); *A61Q 19/00* (2013.01); *C07H 15/06* (2013.01); *C11D 1/42* (2013.01); *C11D 1/525* (2013.01); *C11D 1/662* (2013.01); *C11D 3/227* (2013.01); *C11D 3/48* (2013.01); *C11D 7/329* (2013.01)

(58) Field of Classification Search
CPC .......... C07H 15/203; C11D 7/329; C11D 3/48
USPC ....................................................... 536/17.2
See application file for complete search history.

(56) References Cited

U.S. PATENT DOCUMENTS

| | | | |
|---|---|---|---|
| 4,106,991 A | 8/1978 | Markussen et al. | |
| 4,435,307 A | 3/1984 | Barbesgaard et al. | |

(Continued)

FOREIGN PATENT DOCUMENTS

| | | |
|---|---|---|
| DE | 19634019 A2 | 2/1998 |
| EP | 238216 A1 | 9/1987 |

(Continued)

OTHER PUBLICATIONS

Roncal et al. Carbohydrate Research, 2007, 2750-2756.*

(Continued)

*Primary Examiner* — Brandon Fetterolf
*Assistant Examiner* — Ana Z Muresan
(74) *Attorney, Agent, or Firm* — Shook, Hardy & Bacon L.L.P.

(57) ABSTRACT

A method of preparing a compound of formula (I): wherein: a first group selected from $R^1$, $R^2$ and $R^3$ is an amino- or N-acylamino monosaccharide moiety, the acyl group having 1 to 6 carbon atoms, or an oligosaccharide chain comprising 2 to 4 monosaccharide moieties, at least one of which is an amino- or N-acylamino monosaccharide moiety; a second group selected from $R^1$, $R^2$ and $R^3$ is a alkanoyl and alkenoyl acyl group having 3 to 40 carbon atoms; and a third group selected from $R^1$, $R^2$ and $R^3$ is hydrogen, the method comprising contacting a monoacylglycerol, the acyl moiety thereof being a saturated or unsaturated acyl group having 3 to 40 carbon atoms, or an activated derivative thereof, with a source of amino- or N-acylamino monosaccharide moiety, or an activated derivative thereof, and, if required, a source of unsubstituted monosaccharide moiety, or an activated derivative thereof, optionally in the presence of a suitable catalyst or activating agent, is described.

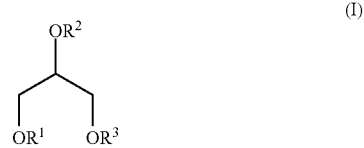

(I)

5 Claims, 18 Drawing Sheets

(51) Int. Cl.
*A61K 8/60* (2006.01)
*A61Q 19/00* (2006.01)
*C07H 15/06* (2006.01)
*C11D 1/42* (2006.01)
*C11D 1/52* (2006.01)
*C11D 1/66* (2006.01)
*C11D 3/22* (2006.01)
*C11D 3/48* (2006.01)
*C11D 7/32* (2006.01)

(56) References Cited

U.S. PATENT DOCUMENTS

| | | |
|---|---|---|
| 4,661,452 A | 4/1987 | Markussen |
| 5,457,046 A | 10/1995 | Woeldike et al. |
| 5,648,263 A | 7/1997 | Schuelein et al. |
| 5,686,593 A | 11/1997 | Woeldike et al. |
| 5,691,178 A | 11/1997 | Schuelein et al. |
| 5,728,661 A | 3/1998 | Petit et al. |
| 5,763,254 A | 6/1998 | Woeldike et al. |
| 5,776,757 A | 7/1998 | Schuelein et al. |
| 6,287,841 B1 | 9/2001 | Mulleners et al. |

FOREIGN PATENT DOCUMENTS

| | | |
|---|---|---|
| EP | 407225 A1 | 1/1991 |
| EP | 218272 B1 | 3/1992 |
| EP | 260105 B1 | 5/1994 |
| EP | 258068 B1 | 8/1994 |
| EP | 531372 B1 | 2/1995 |
| EP | 305216 B1 | 8/1995 |
| EP | 531315 B1 | 3/1997 |
| EP | 331376 B1 | 10/1997 |
| EP | 495257 B1 | 6/2002 |
| GB | 1372034 A | 10/1974 |
| GB | 1483591 A | 8/1977 |
| JP | 64074992 | 3/1989 |
| WO | 8906270 A1 | 7/1989 |
| WO | 8906279 A1 | 7/1989 |
| WO | 8909259 A1 | 10/1989 |
| WO | 9116422 A1 | 10/1991 |
| WO | 9205249 A1 | 4/1992 |
| WO | 9219708 A1 | 11/1992 |
| WO | 9219709 A1 | 11/1992 |
| WO | 9219729 A1 | 11/1992 |
| WO | 9324618 A1 | 12/1993 |
| WO | 9401541 A1 | 1/1994 |
| WO | 9407998 A1 | 4/1994 |
| WO | 9425578 A1 | 11/1994 |
| WO | 9425583 A1 | 11/1994 |
| WO | 9506720 A1 | 3/1995 |
| WO | 9510602 A1 | 4/1995 |
| WO | 9522615 A1 | 8/1995 |
| WO | 9524471 A1 | 9/1995 |
| WO | 9530011 A2 | 11/1995 |
| WO | 9530744 A2 | 11/1995 |
| WO | 9535381 A1 | 12/1995 |
| WO | 9600292 A1 | 1/1996 |
| WO | 9611262 A1 | 4/1996 |
| WO | 9612012 A1 | 4/1996 |
| WO | 9613580 A1 | 5/1996 |
| WO | 9627002 A1 | 9/1996 |
| WO | 9629397 A1 | 9/1996 |
| WO | 9634108 A2 | 10/1996 |
| WO | 9634946 A1 | 11/1996 |
| WO | 9704079 A1 | 2/1997 |
| WO | 9707202 A1 | 2/1997 |
| WO | WO-9713783 * | 4/1997 |
| WO | 9808940 A1 | 3/1998 |
| WO | 9812307 A1 | 3/1998 |
| WO | 9815257 A1 | 4/1998 |
| WO | 9820115 A1 | 5/1998 |
| WO | 9901544 A1 | 1/1999 |
| WO | 9925846 A2 | 5/1999 |
| WO | 0114629 A1 | 3/2001 |
| WO | 0134899 A1 | 5/2001 |

OTHER PUBLICATIONS

Smith et al. Biochem J. 1997, 326, 393-400.*
Chikako Shimizu and Kazuo Achiwa, "Syntheses of Biologically Active Sialosylglycerol Derivatives", Chem Pharm Bull 37(8) 2258-2260 (1989) vol. 37, No. 8.
Patent Abstract of Japan, Publication No. 02225489; Applicant: Mect Corp.
Chikako Shimizu, et al., "Neuraminic Acid Compounds v. Syntheses of Biologically Active Sialoyl-Glycerol Derivatives and Galactosyl-Glycerol Derivative", Chem Pharm Bull 38(12) 3347-3354 (1990).
Jon K. Fairweather, et al., "The Asymmetric Dihydroxylation of Some Alkenyl 2-Acetylamino-2-deoxy-b-D-glucopyranosides: the Preparation of Optically Pure Epoxides as Putative Inhibitors of Chitinases", Aust J. Chem., 1998, 51, 471-482.
Patrick L. Selmair and Peter Koehler, "Baking Performance of Synthetic Glycolipids in Comparison to Commercial Surfactants", J Agric. Food Chem 2008, 56, 6691-6700.
Takashi Nakae, et al., "Foaming Power and Emulsifying Properties of the Hydrolyzates by Lipase . . . ", Biochemical Research Laboratory, Ezaki Glico Co., Ltd., Osaka, 555-8502, Japan (1998).
International Search Report, 3 pp.
Columbo et al., Anti-tumor-promoting effects of glycoglycerolipid analogues on two-stage mouse skin carcinogenesis; Cancer Letters 161 (2000), 201-205; Sep. 18, 2000.
Columbo et al., Inhibitory effects of fatty acid monoesters of 2-O-B-D-Glucosylglycerol of Epstein-Barr virus activation; Cancer Letters 123 (1998) 83-86; Sep. 3, 1997.
Larsen et al., An Antiinflammatory Galactolipid from Rose Hip (*Rosa canina*) that Inhibits Chemotaxis of Human Peripheral Blood Neutrophils in Vitro; J. Nat. Prod. 2003, 66, 994-995; Feb. 12, 2003.
Morimoto et al., Anti-Tumour-Promoting Glyceroglycolipids from the Green Alga, *Chlorella vulgaris*; Faculty of Pharmaceutical Sciences, Nagoya City University, May 15, 1995.
Nagatsu et al., Synthesis and Structure—Anti-Tumor-Promoting Activity Relationship of Monogalactosyl Diacylglycerols; Faculty of Pharmaceutical Sciences, Nagoya City University, May 24, 1994.
Nakata, High Resistance to Oxygen Radicals and Heat is Caused by a Galactocerolipid in *Microbacterium* sp. M874; Central Research Laboratories, Mercian Corporation, Jan. 31, 2000.
Pahlsson et al., Characterization of Galactosyl Glycerolipids in the HT29 Human Colon Carcinoma Cell Line, Department of Diomedicine and Surger, Division of Clinical Chemistry and Departement of Physics and Measurement Technology, Linkoping University, S-581 85 Linkoping, Sweden, Nov. 20, 2001.
Shirahashi et al., Antitumor-Promoting Activities of Various Synthetic 1-O-Acyl-3-O-(6'-O-Acyl-B-D-Galactopyranosyl)-sn-Glycerols Related to Natural Product from Freshwater *Cyanobacterium anabaena* flos-aquae f. flos-aquae; Faculty of Pahrmaceutical Sciences, Nagoya City University (Japan), Mar. 8, 1996, Pharmaceutical Society of Japan, pp. 1404-1406.
Shirahashi et al., Isolation and Identification of Anti-tumor-Promoting Principles form the Fresh-Water Cyanobacterium *Phormidium tenue*, Faculty of Pharmaceutical Sciences, Nagoya City University (Japan), Feb. 22, 1993, Pharmaceutical Society of Japan, pp. 1664-1666.
Janwitayanuchit et al., Synthesis and anti-herpes simplex viral activity of monoglycosyl diglycerides; Faculty of Pharmaceutical Sciences, Chulalongkorn University Bangkok (Thailand), Faculty of Science, Chulalongkorn University Bangkok (Thailand), Aug. 20, 2003, Elsevier Ltd., pp. 1253-1264.
Langworthy et al., A Sulfonolipid and Novel Glucosamidyl Glycolipids From the Extreme Thermoacidophile *Bacillus acidocaldarius*, Department of Microbiology, School of Medicine, University of South Dakota, Dec. 30, 1975, Elsevier Scientific Publishing Company, Amsterdam, pp. 550-569.
Phizackerley et al., 1-(O-B-Glucosaminyl)-2,3-diglyceride in *Bacillus megaterium*; Nuffield Department of Clinical Biochemistry, University of Oxford, Jul. 19, 1971, pp. 499-502.

(56) References Cited

OTHER PUBLICATIONS

Wuts et al., Greene's Protective Groups in Organic Synthesis, 4th Ed., Copyright 2007.
Dayhoff et al., A Model of Evolutionary Change in Proteins; Atlas of Protein Sequence and Structure 1978, vol. 5, Supl. 3, pp. 345-352.
Jones et al., The Rapid Generation of Mutation Data Matrices From Protein Sequences, 1992, Available at: http://www.ncbi.nlm.nih.gov/pubmed/1633570.
Henikoff et al., Amino acid substitution matrices from protein blocks; Howard Hughes Medical Institute, Basic Sciences Division, Fred Hutchinson Cancer Research Center, v. 89, Aug. 28, 1992, pp. 10915-10919.
Gonnet et al., Exhaustive Matching of the Entire Protein Sequence Database; Science, vol. 256, Jun. 5, 1992, pp. 1443-1445.
Higgins et al., CLUSTAL: A Package for Performing Multiple Sequence Alignment on a Microcomputer; Department of Genetics, Trinity College, Dublin 2 (Ireland), Aug. 23, 1988.
Higgins et aL—Clustal V: Improved Software for Multiple Sequence Alignment, CABIOS, vol. 8, No. 2, 1992, Oxford University Press, pp. 189-191.
Thompson et al., CLUSTAL W: improving the sensitivity of progressive multiple sequence alignment through sequence weighting, position-specific gap penalties and weight matrix choice; Nucleic Acids Research, 1994, vol. 22, No. 22, 1994, Oxford University Press, pp. 4673-4680.
Larkin et al., Clustal W and Clustal X version 2.0; Bioinformatics Applications Note, vol. 23, No. 21, 2007, The Author, Oxford University Press, pp. 2947-2948.
Altschul et al., Basic Loyal Alignment Search Tool, J. Mol. Biol. 215, 1990, Acedemic Press Limited, pp. 403-410.

Tatusova et al., BLAST 2 Sequences, a new tool for comparing protein and nucleotide sequences; FEMS Microbiology Letters, 174, 1999, Elsevier Science B.V., pp. 247-250.
Simon et al., Peptoids: A modular approach to drug discovery; Proc. Natl. Acad. Sci. USA, vol. 89, Chemistry, Oct. 1992, pp. 9367-9371.
Horwell, The 'peptoid' approach to the design of non-peptide, small molecule agonists and antagonists of neuropeptides; Trends in Biotechnology, vol. 13, No. 4, Apr. 1995, Elsevier Science Ltd., pp. 132-134.
Roncal et al., High yield production of monomer-free chitosan oligosaccharides by pepsin catalyzed hydrolysis of a high deacetylation degree chitosan; Carbohydrate Research 342, 2007, Elsevier Ltd., pp. 2750-2756.
Neimert-Andersson et al., A Metathesis Approach for the Preparation of Polyhydroxylated Compounds as Head Groups in Surfactant Synthesis; Eur. J. Org. Chem., 2006, Wiley-VCH Verlag GmbH & Co. KGaA, Weinheim, pp. 978-985.
Takashi et al., Foaming power and emulsifying properties of the dydrolyzates by lipase from *Rhizopus arrhizus* on digalactosyldiacylglyceral and trigalactosyldiacylglycerol extractedf rom pumpkin; Food Science Technology, Tokyo, 4 (3), 1998, p. 235-240.
Wu et al., Synthesis of Natural a-6-Dehydroxy-6-aminoglucoglycerolipids; Chinese Journal of Chemistry, 26, 2008, SIOC. CAS. Shanghai & Wiley-VCH Verlug GmbH & Co. KGaA. Weinheim, pp. 1641-1646.
Davis et al., Synthesis and Activation of Carbohydrate Donors: Acetates, Halides, Phenyl selenides and Glycals; Best Synthetic Methods: Carbohydrates, 2003, Elsevier Science Ltd., pp. 69-120.

\* cited by examiner

SEQ ID No. 1

Vvppagtpwgtaydkakaalaklnlqdkvgivsgvgwnggpcvgntspaskisypslclqdgplgvrystgstaftpgvqaastwdvnlirer
gqfigeevkasgihvilgpvagplgktpqggrnwegfgvdpyltgiamgqtingiqsvgvqatakhyilneqelnretissnpddrtlhelytwp
fadavqanvasvmcsynkvnttwacedqytlqtvlkdqlgfpgyvmtdwnaqhttvqsansgldmsmpgtdfngnnrlwgpaltnavnsn
qvptsrvddmvtrilaawyltgqdqagypsfnismvqgnhktnvraiardgivllkndanilplkkpasiavvgsaaiignharnspscndkgc
ddgalgmgwgsgavnypyfvapydaintrassqgtqvtlsntdntssgasaargkdvaivfitadsgegyitvegnagdrnnldpwhngnalv
qavagansnvivvvhsvgaiileqilalpqvkavvwaglpsqesgnalvdvlwgdvspsgklvytiakspndyntrivsggsdsfseglfidyk
hfddanitpryefgyglsytkfnysrlsvlstaksgpatgavvpggpsdlfqnvatvtvdiansgqvtgaevaqlyitypssaprtppkqlrgfakl
nltpgqsgtatfnirrrdlsywdtasqkwvvpsgsfgisvgassrdirltstlsva

FIG. 6

SEQ ID No. 2 mryrtaaalalatgpfaradshstsgasaeavvppagtpwgtaydkakaalaklnlqdkvgivsgvgwnggpcvgntspaskisypslclqdg
plgvrystgstaftpgvqaastwdvnlirergqfigeevkasgihvilgpvagplgktpqggrnwegfgvdpyltgiamgqtingiqsvgvqata
khyilneqelnretissnpddrtlhelytwpfadavqanvasvmcsynkvnttwacedqytlqtvlkdqlgfpgyvmtdwnaqhttvqsansg
ldmsmpgtdfngnnrlwgpaltnavnsnqvptsrvddmvtrilaawyltgqdqagypsfnismvqgnhktnvraiardgivllkndanilplk
kpasiavvgsaaiignharnspscndkgcddgalgmgwgsgavnypyfvapydaintrassqgtqvtlsntdntssgasaargkdvaivfitad
sgegyitvegnagdrnnldpwhngnalvqavagansnvivvvhsvgaiileqilalpqvkavvwaglpsqesgnalvdvlwgdvspsgklv
ytiakspndyntrivsggsdsfseglfidykhfddanitpryefgyglsytkfnysrlsvlstaksgpatgavvpggpsdlfqnvatvtvdiansgq
vtgaevaqlyitypssaprtppkqlrgfaklnltpgqsgtatfnirrrdlsywdtasqkwvvpsgsfgisvgassrdirltstlsva

FIG. 7

SEQUENCE LISTING

<160> NUMBER OF SEQ ID NOS: 2

<210> SEQ ID NO 1
<211> LENGTH: 713
<212> TYPE: PRT
<213> ORGANISM: Trichoderma reesei

<400> SEQUENCE: 1

```
Val Val Pro Pro Ala Gly Thr Pro Trp Gly Thr Ala Tyr Asp Lys Ala
  1               5                  10                  15

Lys Ala Ala Leu Ala Lys Leu Asn Leu Gln Asp Lys Val Gly Ile Val
             20                  25                  30

Ser Gly Val Gly Trp Asn Gly Gly Pro Cys Val Gly Asn Thr Ser Pro
         35                  40                  45

Ala Ser Lys Ile Ser Tyr Pro Ser Leu Cys Leu Gln Asp Gly Pro Leu
     50                  55                  60

Gly Val Arg Tyr Ser Thr Gly Ser Thr Ala Phe Thr Pro Gly Val Gln
 65                  70                  75                  80

Ala Ala Ser Thr Trp Asp Val Asn Leu Ile Arg Glu Arg Gly Gln Phe
                 85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365
```

```
Asn Asp Lys Gly Cys Asp Asp Gly Ala Leu Gly Met Gly Trp Gly Ser
    370                 375                 380
Gly Ala Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
            420                 425                 430
Val Phe Ile Thr Ala Asp Ser Gly Glu Gly Tyr Ile Thr Val Glu Gly
        435                 440                 445
Asn Ala Gly Asp Arg Asn Asn Leu Asp Pro Trp His Asn Gly Asn Ala
    450                 455                 460
Leu Val Gln Ala Val Ala Gly Ala Asn Ser Asn Val Ile Val Val Val
465                 470                 475                 480
His Ser Val Gly Ala Ile Ile Leu Glu Gln Ile Leu Ala Leu Pro Gln
                485                 490                 495
Val Lys Ala Val Val Trp Ala Gly Leu Pro Ser Gln Glu Ser Gly Asn
            500                 505                 510
Ala Leu Val Asp Val Leu Trp Gly Asp Val Ser Pro Ser Gly Lys Leu
        515                 520                 525
Val Tyr Thr Ile Ala Lys Ser Pro Asn Asp Tyr Asn Thr Arg Ile Val
    530                 535                 540
Ser Gly Gly Ser Asp Ser Phe Ser Glu Gly Leu Phe Ile Asp Tyr Lys
545                 550                 555                 560
His Phe Asp Asp Ala Asn Ile Thr Pro Arg Tyr Glu Phe Gly Tyr Gly
                565                 570                 575
Leu Ser Tyr Thr Lys Phe Asn Tyr Ser Arg Leu Ser Val Leu Ser Thr
            580                 585                 590
Ala Lys Ser Gly Pro Ala Thr Gly Ala Val Val Pro Gly Gly Pro Ser
        595                 600                 605
Asp Leu Phe Gln Asn Val Ala Thr Val Thr Val Asp Ile Ala Asn Ser
    610                 615                 620
Gly Gln Val Thr Gly Ala Glu Val Ala Gln Leu Tyr Ile Thr Tyr Pro
625                 630                 635                 640
Ser Ser Ala Pro Arg Thr Pro Pro Lys Gln Leu Arg Gly Phe Ala Lys
                645                 650                 655
Leu Asn Leu Thr Pro Gly Gln Ser Gly Thr Ala Thr Phe Asn Ile Arg
            660                 665                 670
Arg Arg Asp Leu Ser Tyr Trp Asp Thr Ala Ser Gln Lys Trp Val Val
        675                 680                 685
Pro Ser Gly Ser Phe Gly Ile Ser Val Gly Ala Ser Ser Arg Asp Ile
    690                 695                 700
Arg Leu Thr Ser Thr Leu Ser Val Ala
705                 710

<210> SEQ ID NO 2
<211> LENGTH: 744
<212> TYPE: PRT
<213> ORGANISM: Trichoderma reesei

<400> SEQUENCE: 2

Met Arg Tyr Arg Thr Ala Ala Ala Leu Ala Leu Ala Thr Gly Pro Phe
1               5                   10                  15
Ala Arg Ala Asp Ser His Ser Thr Ser Gly Ala Ser Ala Glu Ala Val
            20                  25                  30
```

```
Val Pro Pro Ala Gly Thr Pro Trp Gly Thr Ala Tyr Asp Lys Ala Lys
         35                  40                  45

Ala Ala Leu Ala Lys Leu Asn Leu Gln Asp Lys Val Gly Ile Val Ser
     50                  55                  60

Gly Val Gly Trp Asn Gly Gly Pro Cys Val Gly Asn Thr Ser Pro Ala
 65                  70                  75                  80

Ser Lys Ile Ser Tyr Pro Ser Leu Cys Leu Gln Asp Gly Pro Leu Gly
                 85                  90                  95

Val Arg Tyr Ser Thr Gly Ser Thr Ala Phe Thr Pro Gly Val Gln Ala
                100                 105                 110

Ala Ser Thr Trp Asp Val Asn Leu Ile Arg Glu Arg Gly Gln Phe Ile
         115                 120                 125

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
                180                 185                 190

Leu Asn Glu Gln Glu Leu Asn Arg Glu Thr Ile Ser Ser Asn Pro Asp
                195                 200                 205

Asp Arg Thr Leu His Glu Leu Tyr Thr Trp Pro Phe Ala Asp Ala Val
         210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
                260                 265                 270

Thr Thr Val Gln Ser Ala Asn Ser Gly Leu Asp Met Ser Met Pro Gly
         275                 280                 285

Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
                340                 345                 350

Asn Val Arg Ala Ile Ala Arg Asp Gly Ile Val Leu Leu Lys Asn Asp
         355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
                420                 425                 430

Arg Ala Ser Ser Gln Gly Thr Gln Val Thr Leu Ser Asn Thr Asp Asn
         435                 440                 445
```

```
Thr Ser Ser Gly Ala Ser Ala Ala Arg Gly Lys Asp Val Ala Ile Val
    450             455                 460

Phe Ile Thr Ala Asp Ser Gly Glu Gly Tyr Ile Thr Val Glu Gly Asn
465             470                 475                 480

Ala Gly Asp Arg Asn Asn Leu Asp Pro Trp His Asn Gly Asn Ala Leu
            485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
            565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
    610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Lys Gln Leu Arg Gly Phe Ala Lys Leu
            675                 680                 685

Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740
```

METHODS FOR PRODUCING AMINO-SUBSTITUTED GLYCOLIPID COMPOUNDS

CROSS-REFERENCE TO RELATED APPLICATIONS

This application claims priority to PCT Application No. PCT/IB2011/050258 entitled "Methods For Producing Amino-Substituted Glycolipid Compounds," filed Jan. 20, 2011, which claims priority to U.S. Provisional Application No. 61/298,760, filed Jan. 27, 2010 and EP No. 10151489.1, filed Jan. 22, 2010, all of which are expressly incorporated by reference herein in their entirety.

SEQUENCE LISTING

A text file in compliance with ASCII and having a ".txt" extension has been electronically submitted via EFS-Web. The text file named "Sequence Listing" was created on Jun. 29, 2012, and is 12,831 bytes. The text file is expressly incorporated by reference herein in its entirety.

FIELD OF THE INVENTION

This invention relates to a series of amino-substituted glycolipid compounds. It also relates to methods for their preparation and their use in a number of applications, particularly as surfactants and emulsifiers.

BACKGROUND TO THE INVENTION

Glycoglycerolipids or glycolipids are a class of lipids found in nature. The compounds contain most frequently one or two monosaccharide units linked glycosidically to mono- or diacylglycerol. Glycolipids with three or four monosaccharide units are also known. They are especially important in higher plants, algae and bacteria where they are located in photosynthetic membranes, they are less pronounced in animals.

Glucoglycerolipids have physical as well as biological properties that make them an interesting component in food production, and several health-promoting properties have been reported, such as inhibition of tumour growth in the gastro intestinal tract (GIT), anti-inflammatory as well as antiviral effects: see Colombo, D, et al. *Cancer Letters* (Shannon, Ireland), (2000) 161, 201-205; Colombo, D., et al. *Cancer Letters* (Shannon, Ireland), (1998) 123, 233; Larsen, E., et al; *J. Nat. Prod.* (2003) 66, 994-995. Morimoto, A., et al. *Phytochemistry*, (1995) 40, 1433-1437; Nagatsu, A., et al. *Bioorg. Med. Chem. Lett.*, 1994, 4, 1619-1622; Nakata, K. *J. Biochem.* (Tokyo), (2000), 127, 731-737; Pahlsson, P., et al. *Arch. Biochem. Biophys.* (2001) 396, 187-198; Shirahashi, H., et al. *Chem. Pharm. Bull.*, 1996, 44, 1404-1406; Shirahashi, H., et al. *Chem. Pharm. Bull.*, 1993, 41, 1664-1666; and Janwitayanuchit, W., et al, *Phytochemistry* (Elsevier), (2003), 64, 1253-1264.

Langworthy, T. A., et al. *Biochimica et Biophysica Acta*, (1976), 431, 550-569, describe the isolation of glucosamidyl glycolipids from an extreme thermoacidophile *Bacillus acidocaldarius*. The major compound, which comprises about 64% of the total lipids, appears to be a fatty N-acyl derivative of glucopyranosyl(1→4)glucosamine(1→3)-diacylglycerol. The amide-linked fatty acid was primarily branched heptadecanoic, but also 11-cyclohexylundecanoic or 13-cyclohexyltridecanoic acid. A minor product was tentatively identified as O-β-D-glucopyranosyl-(1→4)-O-2-acylamido-2-deoxy-β-D-glucopyranosylmonoacylglycerol.

In bacteria and algae a large number of glycolipids containing different sugar combinations have been reported. For example, 1-(O-β-glucosaminyl)-2,3-diglycerides have been identified in *Bacillus megaterium*: see Phizackerley, P. J. R., et al. *Biochem. J.*, 1972, 126, 499. It constitutes about 5% of the total lipid glucosaminide in the organism and was separated from other lipids by chromatography. The lipid contained glycerol, fatty acids and glucosamine in the molar proportion 1:2:1. The fatty acids were bound by an ester linkage. Partial acid hydrolysis or alkaline hydrolysis of the lipid yields 1-(O-β-glucosaminyl)glycerol.

Shimizu, C. et al. *Chem. Pharm. Bull.* 1989, 37(8), 2258-2260 and *Chem. Pharm. Bull.* 1990, 38(12), 3347-3354, describe sialosylglycerol derivatives and their synthesis. In these compounds, an N-acylamino group is present in place of the hydroxyl group at the 4-position of the monosaccharide moiety (the point of attachment to the glycerol moiety being the 1-position).

JP 2-225489A describes glyceride derivatives having a monosaccharide group bonded at its 1-position to a glycerol moiety. These compounds also have an N-acylamino group in place of the hydroxyl group at the 4-position of the monosaccharide moiety.

Wu et al., Chin. *J. Chem.*, 2008, 26, 1641-1646, describes the synthesis of natural α-6-dehydroxy-6-aminoglucoglycerolipids. The synthetic route involves the intermediate 3-O-(2',3,4'-tri-O-benzyl-6-dehydroxy-6'-benzyloxycarbonylamino-α-D-glucopyranosyl)-1-O-palmitoylglycerol.

Fairweather, J. K. et al., *Aust. J. Chem.*, 1998, 51, 471-482, describes the asymmetric dihydroxylation of alkenyl 2-acetylamino-2-deoxy-β-D-glucopyranosides. The synthetic route involves the intermediate (3'S)-4'-benzoyloxy-3'-hydroxybutyl 3,4,6-tri-O-acetyl-2-acetylamino-2-deoxy-β-glucoside.

DE 19634019 A1 describes glycoglycerolipids and their use as antimicrobials.

Anionic and cationic surface-active solutions are used in a number of applications such as detergents and emulsifiers.

SUMMARY OF THE INVENTION

This invention describes the synthesis of charged biofriendly surface-active molecules by reacting monoglycerides with a source of amino- or N-acylamino monosaccharide moieties, preferably glucosamine or N-acetylglucosamine moieties or any mixtures thereof. The cationic molecules can be produced by making the glycoside from a number of different monoglycerides and amino- or N-acylamino monosaccharide sources. The molecules can be generated via chemical synthesis or via enzymatic transfer of an amino- or N-acylamino monosaccharide moiety from substrates such as chitosan or chitin or chitosan oligomer or chitin oligomer, which acts as a source of glucosamine units, to a monoglyceride.

Accordingly, there is provided according to one aspect of the present invention a compound of formula (I):

wherein:
a first group selected from $R^1$, $R^2$ and $R^3$ is an amino- or N-acylamino monosaccharide moiety, the acyl group having 1 to 6 carbon atoms, or an oligosaccharide chain comprising 2 to 4 monosaccharide moieties, at least one of which is an amino- or N-acylamino monosaccharide moiety; a second group selected from $R^1$, $R^2$ and $R^3$ is a saturated or unsaturated acyl group having 3 to 40 carbon atoms; and a third group selected from $R^1$, $R^2$ and $R^3$ is hydrogen;
with the exception of an O-β-D-glucopyranosyl-(1→4)-O-2-acylamido-2-deoxy-β-D-glucopyranosylmonoacylglycerol.

In some embodiments, there is provided a compound of formula (I) as defined above, with the exception of (3'S)-4'-benzoyloxy-3'-hydroxybutyl 3,4,6-tri-O-acetyl-2-acetylamino-2-deoxy-β-glucoside.

In some embodiments, there is provided a compound of formula (I) as defined above, with the exception of 3-O-(2', 3,4'-tri-O-benzyl-6-dehydroxy-6'-benzyloxycarbonylamino-α-D-glucopyranosyl)-1-O-palmitoylglycerol.

In some embodiments, there is provided a compound of formula (I'):

wherein:
a first group selected from $R^1$, $R^2$ and $R^3$ is an amino- or N-acylamino hexose moiety, the amino or N-acylamino group being present in place of the hydroxyl group at the 2-position of the hexose moiety, the acyl moiety of the N-acylamino group having 1 to 6 carbon atoms, or an oligosaccharide chain comprising 2 to 4 monosaccharide moieties, at least one of which is an amino- or N-acylamino hexose moiety as defined above; a second group selected from $R^1$, $R^2$ and $R^3$ is an alkanoyl group having 3 to 40 carbon atoms or an alkenoyl group having 3 to 40 carbon atoms and 1 to 5 double bonds; and a third group selected from $R^1$, $R^2$ and $R^3$ is hydrogen;
with the exception of an O-β-D-glucopyranosyl-(1→4)-O-2-acylamido-2-deoxy-β-D-glucopyranosylmonoacylglycerol.

There is provided according to another aspect of the present invention a method of preparing a compound of formula (I) or (I') as defined above, comprising contacting a monoacylglycerol, the acyl moiety thereof being a saturated or unsaturated acyl group having 3 to 40 carbon atoms, or an activated derivative thereof, with a source of amino- or N-acylamino monosaccharide moiety or an activated derivative thereof, and, if required, a source of unsubstituted monosaccharide moiety, or an activated derivative thereof, optionally in the presence of a suitable catalyst or activating agent.

In particular, there is provided according to a preferred aspect of the present invention a method of preparing a compound of formula (I) or (I') as defined above, comprising treating a monoacylglycerol, the acyl moiety thereof being a saturated or unsaturated acyl group having 3 to 40 carbon atoms, with a source of amino- or N-acylamino monosaccharide moiety and, if required, a source of unsubstituted monosaccharide moiety, and a transglycosidase enzyme.

In addition, there is provided according to another aspect of the present invention a method for in situ generation of a compound of formula (I) or (I') as defined above in a composition, the composition comprising the following components:

(i) a monoacylglycerol, the acyl moiety thereof being a saturated or unsaturated acyl group having 3 to 40 carbon atoms, or an activated derivative thereof;
(ii) a source of amino- or N-acylamino monosaccharide moiety, or an activated derivative thereof;
(iii) if required, a source of unsubstituted monosaccharide moiety, or an activated derivative thereof; and
(iv) if required, a suitable catalyst or activating agent; the method comprising adding to the composition any of components (i) and (ii) that are not already present in the composition and, if required (iii) and/or (iv) that are not already present in the composition, and allowing the components to react.

There is also provided according to the present invention a foodstuff comprising a compound of the invention or produced by a method of the invention.

There is additionally provided according to the present invention a detergent composition comprising a compound of the invention or produced by a method of the invention.

According to a further aspect of the invention, there is provided use of the above compounds as an emulsifier.

According to a yet further aspect of the invention, there is provided use of the above compounds as a surfactant.

According to a still further aspect of the invention, there is provided use of the above compounds as an antimicrobial agent.

DETAILED DESCRIPTION

Definitions

Monosaccharides and Amino/N-Acylamino Monosaccharides

In the present application, the term "monosaccharide" in its broadest sense means a carbohydrate moiety that cannot be further hydrolysed into simpler carbohydrates. The term is intended to cover in its broadest sense both free monosaccharides and monosaccharide moieties attached (preferably via a glycosidic bond) to other parts of a molecule (either in the starting material, the product or any intermediate) such as glycerol, acyl groups and other monosaccharide moieties. The term is also intended to cover in its broadest sense both unsubstituted monosaccharides (ie where all of the hydroxyl groups normally present in that monosaccharide are present, none being replaced by another functional group) and substituted monosaccharides (such as amino- and N-acylamino monosaccharides, oxidised monosaccharides and deoxymonosaccharides), defined in more detail below.

The monosaccharide moiety may have the D- or L-configuration. Furthermore, the monosaccharide moiety may be an aldose or ketose moiety.

Suitably, the monosaccharide moiety may have 3 to 7, preferably 4 to 6, more preferably 5 or 6, carbon atoms. In one embodiment, the monosaccharide moiety is a hexose moiety (ie it has 6 carbon atoms), examples of which include aldohexoses such as glucose, galactose, allose, altrose, mannose, gulose, idose and talose and ketohexoses such as fructose and sorbose. Preferably, the hexose moiety is a glucose moiety. In another embodiment, the monosaccharide unit is a pentose moiety (ie it has 5 carbon atoms), such as ribose, arabinose, xylose or lyxose.

In one embodiment, the monosaccharide moiety be a deoxy monosaccharide moiety, ie a monosaccharide moiety where one or more (preferably 1 or 2, more preferably only 1) of the hydroxyl groups is replaced with a hydrogen atom. In other embodiments the monosaccharide is not a deoxy monosaccharide and none of the hydroxyl groups is replaced with a hydrogen atom.

In one embodiment, one or more primary hydroxyl groups on the monosaccharide moiety may be oxidised to form a carboxylic acid (—$CO_2H$) group. This group may form salts with a suitable base: examples of such salts are well known to those skilled in the art and include alkali metals such as lithium, sodium and potassium, alkaline earth metals such as magnesium and calcium, and ammonium or mono-, di-, tri- and tetraalkylammonium. In other embodiments the monosaccharide is not an oxidised monosaccharide and none of the primary hydroxyl groups is oxidised to a —$CO_2H$ group.

The term "amino monosaccharide" means a monosaccharide, as defined above, which contains at least one amine (—$NR_2$) group (wherein each group R is independently hydrogen or $C_{1-6}$ alkyl) in place of the corresponding number of hydroxyl groups of the monosaccharide. The term is intended to cover in its broadest sense both free amino monosaccharides and amino monosaccharide moieties attached (preferably via a glycosidic bond) to other parts of a molecule (either in the starting material, the product or any intermediate) such as acyl groups, glycerol moieties and other monosaccharide moieties (which may be unsubstituted monosaccharide moieties or substituted monosaccharide moieties such as further mino- or N-acylamino substituted monosaccharide moieties).

In the amine group $NR_2$, each group R is independently hydrogen or $C_{1-6}$ alkyl (as defined below). The groups R may be the same or different. Preferably each group R is independently hydrogen or $C_{1-4}$ alkyl, more preferably hydrogen, methyl or ethyl, and most preferably hydrogen or methyl. In a particularly preferred embodiment, both groups R are hydrogen.

In the definition of the amine group $NR_2$ above, the term 'alkyl' means a straight or branched monovalent saturated hydrocarbon chain containing from 1 to 6 carbon atoms. Examples of alkyl groups include methyl, ethyl, n-propyl, i-propyl, n-butyl, i-butyl, sec-butyl, t-butyl, n-pentyl, i-pentyl, neopentyl, n-hexyl and i-hexyl. Preferably, 'alkyl' is $C_{1-4}$ alkyl, and most preferably methyl or ethyl.

The term "N-acylamino monosaccharide" means an amino-monosaccharide, as defined above, wherein an acyl group R'—C(=O)— (where R' is hydrogen or a $O_{1-5}$ alkyl group as defined above) is present in place of one of the groups R on the amine group. In other words, the term "N-acylamino monosaccharide" means a monosaccharide, as defined above, which contains at least one acylamino (—NR—C(=O)—R') group (wherein R is as defined above) in place of the corresponding number of hydroxyl groups of the monosaccharide. The acyl group R'—C(=O)— in the definition of the N-acylamino group has a total of 1 to 6 carbon atoms (including the carbonyl carbon). Examples of suitable acyl groups include methanoyl (formyl), ethanoyl (acetyl), propanoyl, butanoyl, pentanoyl and hexanoyl. Preferably, the acyl group has 2 to 4 carbon atoms. More preferably, the acyl group is acetyl.

The amino- or N-acylamino monosaccharide moiety may have the D- or L-configuration. Furthermore, the amino- or N-acylamino monosaccharide moiety may be an amino- or N-acylamino aldose or aminoketose moiety.

Suitably, the amino- or N-acylamino monosaccharide moiety may have 5 to 7, preferably 5 to 6, carbon atoms. In a preferred embodiment, the amino- or N-acylamino monosaccharide moiety is an amino or N-acylamino hexose moiety (ie it has 6 carbon atoms), examples of which include amino- or N-acylamino aldohexoses such as amino- or N-acylamino substituted glucose, galactose, allose, altrose, mannose, gulose, idose and talose and amino- or N-acylamino ketohexoses such as amino- or N-acylamino substituted fructose and sorbose. Preferably, the amino- or N-acylamino hexose moiety is an amino- or N-acylamino glucose moiety.

The number of amino or N-acylamino groups on the amino- or N-acylamino monosaccharide moiety is limited only by the number of replaceable hydroxyl groups on the monosaccharide. Suitably, the amino-substituted monosaccharide moiety contains 1 to 3, preferably 1 or 2, more preferably only one amino group or N-acylamino group in place of the corresponding number of hydroxyl groups of the monosaccharide.

The amino or N-acylamino group(s) may be present in place of any of the hydroxyl groups on the monosaccharide moiety. For example, they may be present at the 2-, 3-, 4-, 5- or 6-position (the monosaccharide being connected to the glycerol portion of the molecule at the 1-position). However it is preferred that when the amino- or N-acylamino monosaccharide moiety is an amino or N-acylamino hexose moiety, the amino or N-acylamino group is present in place of the hydroxyl group at the 2-position of the hexose moiety.

Examples of amino- or N-acylamino monosaccharides include the following:

amino or N-acylamino pentoses such as 2-amino-2-deoxy-(D or L)-arabinose, 3-deoxy-3-(methylamino)-L-arabinose (4-epi-gentosamine), 2,4-diamino-2,4-dideoxy-L-arabinose, 2,3,5-triamino-2,3,5-trideoxy-D-arabinoic acid, 2-amino-2-deoxy-D-ribose, 2-amino-2-deoxypentofuranose, 3-amino-3-deoxy-D-ribose, 2-amino-2-deoxy-D-xylose, 3-deoxy-3-(methylamino)-D-xylose (gentosamine) and 5-amino-5-deoxypentofuranose;

amino or N-acylamino hexoses, for example amino or N-acylamino alloses and amino or N-acylamino altroses, such as 2-amino-2-deoxy-D-allose (D-allosamine), 3,6-dideoxy-3-(dimethylamino)-D-altrose (ravidosamine); amino or N-acylamino galactoses such as 2-amino-2-deoxy-D-galactose (chondrosamine, D-galactosamine), 2,6-dideoxy-2-(methylamino)-D-galactose (methylfucosamine), 4-amino-4,6-dideoxy-D-galactose (thomosamine), 4,6-dideoxy-4-(methylamino)-D-galactose, 2,4-diamino-2,4,6-trideoxy-D-galactose, amino or N-acylamino glucoses such as 2-amino-2-deoxy-D-glucose (D-glucosamine, chitosamine), 2-(acetylamino)-2-deoxy-D-glucose (N-acetylglucosamine) 2-amino-2-deoxy-L-glucose, 2-deoxy-2-(methylamino)-L-glucose, 2-amino-2,6-dideoxy-D-glucose (D-quinovosamine), 3-amino-3-deoxy-D-glucose (kanasamine), 3,6-dideoxy-3-(dimethylamino)-D-glucose (mycaminose), 4-amino-4-deoxy-D-glucose, 4-amino-4,6-dideoxy-D-glucose (viosamine), 4,6-dideoxy-4-(methylamino)-D-glucose (bamosamine), 4,6-dideoxy-4-(dimethylamino)-D-glucose (amosamine), 4-amino-4-deoxy-D-glucuronamide, 6-amino-6-deoxy-D-glucose, 2,6-diamino-2,6-dideoxy-D-glucose (neosamine C); amino or N-acylamino guloses, amino or N-acylamino idoses and amino or N-acylamino mannoses such as 2-amino-2-deoxy-D-gulose (D-gulosamine), 2-deoxy-2-(methylamino)-D-gulose, 2-amino-2-deoxy-L-gulose (L-gulosamine), 2,6-diamino-2,6-dideoxy-L-idose (neosamine B, paromose), 3-amino-3,6-dideoxy-D-mannose (mycosamine), 4-amino-4,6-dideoxy-D-mannose (perosamine), or other amino or N-acylamino hexoses such as 2-amino-2,3-dideoxy-D-ribo-hexose, 3-amino-2,3,6-trideoxy-D-arabino-hexose (D-acosamine), 3-amino-2,3,6-trideoxy-L-arabino-hexose (L-acosamine), 3-amino-2,3,6-trideoxy-3-C-methyl-L-arabino-hexose (4-epi-vancosamine), 3-amino-2,3,6-trideoxy-L-lyxo-hexose (L-daunosamine), 2,3,6-trideoxy-3-(methylamino)-L-lyxo-hexose (2,3,6-trideoxy-3-(dimethylamino)-L-lyxo-hexose (L-rhodosamine), 2,3,6-trideoxy-3-(dimethylamino)-D-xylo-hexose (D-angolosamine), 3-amino-2,3,6-trideoxy-L-ribo-hexose (ristosamine), 2,3,6-trideoxy-3-(dimethylamino)-L-ribo-hexose (L-megosamine), 3,4,6-trideoxy-3-(dimethylamino)-D-xylo-hexose (desosamine), 4-amino-2,3,4,6-tetradeoxy-L-erythro-hexose (tolyposamine), 2,3,4,6-tetradeoxy-4-(dimethylamino)-D-erythro-hexose (forosamine), 2,4-diamino-2,3,4,6-tetradeoxy-D-arabino-hexose (kasugamine), 2,6-diamino-2,3,6-trideoxy-D-ribo-hexose (nebrosamine, tobrosamine), 2,6-diamino-2,4,6-trideoxy-D-xylo-hexose, 2,6-diamino-2,3,4,6-tetradeoxy-D-erythro-hexose (purpurosamine C) and 2,6-diamino-2,3,4,6-tetradeoxy-6-N-methyl-D-erythro-hexose;
amino or N-acylamino heptoses, such as 2-amino-2,7-dideoxy-D-glycero-D-gluco-heptose, 4-amino-4-deoxy-(D or L)glycero-D-gluco-heptose, 4-amino-4-deoxy-(D or L)-glycero-D-manno-heptose, 6-amino-6,7-dideoxy-D-glycero-D-gluco-heptose, 2,6-diamino-2,3,4,6,7-pentadeoxy-L-lyxo-heptose (6-epi-purpurosamine B), 2,6-diamino-2,3,4,6,7-pentadeoxy-D-ribo-hept-4-enopyranose, 2,6-diamino-2,3,4,6,7-pentadeoxy-D-ribo-heptose (purpurosamine B) and 2-amino-2,3,4,6,7-pentadeoxy-6-(methylamino)-D-ribo-heptose (purpurosamine A).

In the compounds of the present invention, the degree of acylation of the amino monosaccharide moiety or moieties may vary from 0 (ie no amino groups are acylated) to 1 (ie all amino groups are acylated). The preferred degree of acylation depends on the required functionality and intended use of the finished product: compounds intended for use as cationic emulsifiers require a low degree of acylation (in order for sufficient basic —$NR_2$ groups to be available for protonation), whereas neutral compounds require a high degree of acylation to ensure an excess of basic groups are not present. Preferably, the degree of acylation of the amino monosaccharide moiety or moieties ranges from 0.05 to 0.8.

In the compounds of the present invention, the amino- or N-acylamino monosaccharide moiety may be bonded via a glycosidic linkage to one or more (a) a further amino- or N-acylamino monosaccharide moiety (as defined and exemplified above) and/or one or more (b) an unsubstituted monosaccharide moiety, as defined above to form an oligosaccharide chain having 2 to 4 monosaccharide moieties. In this embodiment, at least one of the monosaccharide moieties forming the oligosaccharide chain must be the amino- or N-acylamino monosaccharide moiety. Preferably 1 or 2, more preferably only 1, one of the monosaccharide moieties forming the oligosaccharide chain is an amino- or N-acylamino monosaccharide moiety. The amino- or N-acylamino monosaccharide moiety or moieties may be present at any position on the oligosaccharide chain. However, it is preferred that one amino- or N-acylamino monosaccharide moiety is bonded to the glycerol backbone.

It is preferred in the compounds of the present invention that the amino- or N-acylamino monosaccharide moiety is the only monosaccharide moiety present on the molecule, i.e. it is not attached either to an unsubstituted monosaccharide moiety or to a further amino- or N-acylamino monosaccharide moiety.

Preferably, the amino- or N-acylamino monosaccharide moiety is selected from glucosamine or N-acetylglucosamine.

Acyl Groups

The term 'acyl group' (particularly, although not exclusively, in the definition of the second group of the compounds of the present invention) means a straight- or branched chain, saturated or unsaturated, group of the formula R—C(═O)— wherein R is a hydrocarbyl group. Typically, such acyl groups have a total of 3 to 40 carbon atoms, preferably 6 to 30 carbon atoms, such as at least 8 to 24 carbon atoms, for example 10 to 22, for example 10, 12, 14, 16 or 18 carbon atoms. In one particular embodiment, such an acyl group is an alkanoyl group (ie a fully saturated, fully aliphatic group where the group R is alkyl). Alternatively, such an acyl group comprises an alkenoyl group (ie an unsaturated, fully aliphatic group where the group R is alkenyl, ie an unsaturated aliphatic group containing one or more double bonds): such a group may have, for example, 1 to 5 double bonds, preferably 1, 2 or 3 double bonds, more preferably 1 or 2 double bonds.

Examples of acyl groups include saturated acyl groups, for example alkanoyl groups such as butanoyl (butyryl), hexanoyl (caproyl), octanoyl (capryl), decanoyl (caprinyl), dodecanoyl (lauroyl), tetradecanoyl, (myristoyl), hexadecanoyl (palmitoyl), octadecanoyl (stearoyl), eicosanoyl (arachidonyl), docosanoyl (behenoyl) and tetracosanoyl (lignoceroyl) groups, and unsaturated acyl groups, for example alkenoyl groups such as cis-tetradec-9-enoyl (myristoleyl), cis-hexadec-9-enoyl (palmitoleyl), cis-octadec-9-enoyl (oleyl), cis cis-9,12-octadecadienoyl (linoleyl), cis,cis,cis-9,12,15-octadecatrienoyl (linolenyl), cis,cis,cis-6,9,12-octadecatrienoyl (gamoleyl), and cis,cis,cis,cis-5,8,11,14-eicosa-tetraenoyl (arachidonyl) groups.

In this aspect, preferred acyl groups are saturated or unsaturated (preferably saturated) acyl groups having 6 to 24 carbon atoms. More preferred acyl groups are saturated or unsaturated acyl groups having 8 to 18 carbon atoms, especially the n-decanoyl (caprinyl), n-dodecanoyl (lauroyl), n-tetradecanoyl (myristoyl), n-hexadecanoyl (palmitoyl), n-octadecanoyl (stearoyl), cis-octadec-9-enoyl (oleyl), cis,cis-9,12-octadecadienoyl (linoleyl) and cis,cis,cis-9,12,15-octadecatrienoyl (linolenyl) groups. Especially preferred are the n-decanoyl group and n-octadecanoyl groups.

In one aspect, the acyl group is an alkanoyl group having a total of 3 to 40 carbon atoms, preferably 6 to 30 carbon atoms, such as 8 to 24 carbon atoms. In one embodiment, the acyl group is an alkanoyl group having a total of 8 to 18 carbon atoms, for example 8, 10, 12, 14, 16 or 18 carbon atoms.

In one aspect, the acyl group is an alkenoyl group having a total of 3 to 40 carbon atoms, preferably 6 to 30 carbon atoms, such as 8 to 24 carbon atoms and 1 to 5, preferably 1, 2 or 3, more preferably 1 or 2 double bonds. In one embodiment, the acyl group is an alkenoyl group having a total of 8 to 18 carbon atoms, for example 8, 10, 12, 14, 16 or 18 carbon atoms and 1 to 3 double bonds.

In the compounds of the present invention, a first group selected from $R^1$, $R^2$ and $R^3$ (preferably selected from $R^1$ and $R^3$) is an amino- or N-acylamino monosaccharide moiety, the acyl group having 1 to 6 carbon atoms, or an oligosaccharide chain comprising 2 to 4 monosaccharide moieties, at least one of which is an amino- or N-acylamino monosaccharide moiety.

More preferably, the first group is an amino- or N-acylamino monosaccharide moiety, the acyl group having 1 to 6 carbon atoms. In other words, it is preferred that this amino- or N-acylamino monosaccharide moiety is the only monosaccharide moiety present on the molecule, and it is not bonded to a further unsubstituted monosaccharide or amino- or N-acylamino monosaccharide moiety.

Preferably, the first group is an amino- or N-acylamino hexose moiety, the acyl group having 2 to 4 carbon atoms. In this embodiment, the amino or N-acylamino group is preferably present at the 2-position of the hexose moiety.

In an especially preferred embodiment, the first group is selected from glucosamine or N-acetylglucosamine.

In the compounds of the present invention, a second group selected from $R^1$, $R^2$ and $R^3$ (preferably selected from $R^1$ and $R^3$) is preferably a saturated or unsaturated acyl group (preferably an alkanoyl or alkenoyl group) having 3 to 40 carbon atoms. Preferably, the second group is a saturated or unsaturated acyl group (preferably an alkanoyl or alkenoyl group) having 6 to 24 carbon atoms. More preferably, the second group is a saturated or unsaturated (preferably saturated) acyl group (preferably an alkanoyl group) having 8 to 18 carbon atoms, especially 10, 12, 14, 16 or 18 carbon atoms. Even more preferably, the second group is n-decanoyl, n-dodecanoyl, n-tetradecanoyl, n-hexadecanoyl, n-octadecanoyl, cis-octadec-9-enoyl (oleyl), cis,cis-9,12-octadecadienoyl (linoleyl) or cis,cis,cis-9,12,15-octadecatrienoyl (linolenyl).

In an especially preferred embodiment, the second group is n-decanoyl or n-octadecanoyl.

In the compounds of the present invention, a third group selected from $R^2$ and $R^3$ is hydrogen. Preferably, $R^2$ is hydrogen.

Preferred according to the present invention are compounds wherein:
a first group selected from $R^1$ and $R^3$ is an amino- or N-acylamino monosaccharide moiety, the acyl group having 1 to 6 carbon atoms, or an oligosaccharide chain comprising 2 to 4 monosaccharide moieties, at least one of which is an amino- or N-acylamino monosaccharide moiety;
a second group selected from $R^1$ and $R^3$ is a saturated or unsaturated acyl group (preferably an alkanoyl or alkenoyl group) having 3 to 40 carbon atoms; and
$R^2$ is hydrogen.

Especially preferred according to the present invention are compounds wherein:
the first group (preferably selected from $R^1$ and $R^3$) is an amino- or N-acylamino monosaccharide moiety, the acyl group having 1 to 6 carbon atoms; and
the second group (preferably selected from $R^1$ and $R^3$) is a saturated or unsaturated acyl group (preferably an alkanoyl or alkenoyl group) having 6 to 24 carbon atoms.

Particularly preferred according to the present invention are compounds wherein:
the first group (preferably selected from $R^1$ and $R^3$) is an amino- or N-acylamino hexose moiety, the acyl group having 2 to 4 carbon atoms; and
the second group (preferably selected from $R^1$ and $R^3$) is a saturated or unsaturated acyl group (preferably an alkanoyl or alkenoyl group) having 8 to 18 carbon atoms.

Even more preferred according to the present invention are compounds wherein:
the first group (preferably selected from $R^1$ and $R^3$) is selected from glucosamine or N-acetylglucosamine; and
the second group (preferably selected from $R^1$ and $R^3$) is selected from n-decanoyl, n-dodecanoyl, n-tetradecanoyl, n-hexadecanoyl, n-octadecanoyl, cis-octadec-9-enoyl (oleyl), cis,cis-9,12-octadecadienoyl (linoleyl) or cis,cis,cis-9,12,15-octadecatrienoyl (linolenyl).

Particularly preferred compounds of the present invention are selected from:
1-O-(2-amino-2-deoxy-β-D-glucopyranosyl)-3-n-decanoylglycerol;
1-O-(2-(acetylamino)-2-deoxy-β-D-glucopyranosyl)-3-n-decanoylglycerol; and
1-O-(2-amino-2-deoxy-β-D-glucopyranosyl)-3-n-octadecanoylglycerol.

Methods

The compounds of the present invention may be prepared by a number of methods generally known to those skilled in the art. Generally, the compounds may be prepared by contacting a monoacylglycerol, the acyl moiety thereof being a saturated or unsaturated acyl group having 3 to 40 carbon atoms, or an activated derivative thereof, with a source of amino- or N-acylamino monosaccharide moiety or an activated derivative thereof, and, if required, a source of unsubstituted monosaccharide moiety, or an activated derivative thereof, optionally in the presence of a suitable catalyst or activating agent.

When the compounds of the present invention include an oligosaccharide chain, such compounds can also be formed by reacting a compound of the present invention having one monosaccharide moiety fewer than the target compound, with a source of amino- or N-acylamino monosaccharide moiety or an activated derivative thereof, to add this amino- or N-acylamino unsubstituted monosaccharide to the chain. It is therefore envisaged within the scope of the present invention that compounds of the present invention may function as intermediates for the production of further compounds of the present invention having one monosaccharide or amino- or N-acylamino monosaccharide more than the intermediate compound.

The compounds of the present invention may be generated in situ (ie in the composition in which they are intended to be used), for example in a foodstuff or feedstuff or in a detergent or laundry composition. This aspect is described in more detail below.

Monoglycerides (Monoacylglycerols)

One of the starting materials for preparing the compounds of the present is a monoglyceride. In this specification the term 'monoglyceride' (also known as monoacylglycerol) means a compound comprising one acyl group (as defined and exemplified above) covalently bonded to a glycerol moiety via an ester linkage (the other two OH groups of the glycerol part being free to form a glycosidic bond with the amino- or N-acylamino-substiuted monosaccharide). It is envisaged within the scope of the present invention that the lipid acceptor may comprise a mixture of monoglycerides.

The acyl group of the monoglyceride may be present on any one of the three carbons of the glycerol molecule: it is therefore envisaged within the scope of the present invention that the monoglyceride may comprise a 1-monoacylglycerol, a 2-monoacylglycerol, or a mixture thereof. Preferably, the monoglyceride is a 1-monoacylglycerol. When a mixture of monoglycerides is present, the mixture suitably comprises at least 50%, preferably at least 60%, more preferably at least 70%, even more preferably at least 80%, still more preferably at least 90%, yet more preferably at least 95%, still more preferably at least 97%, and most preferably at least 99%, 1-monoacylglycerol (by weight).

Suitably, the acyl moiety of the monoacylglycerol is a saturated or unsaturated acyl group (preferably an alkanoyl or alkenoyl group) having 6 to 24 carbon atoms. Preferably, the acyl moiety of the monoacylglycerol is a saturated or unsaturated acyl group (preferably an alkanoyl or alkenoyl group) having 8 to 18 carbon atoms. Even more preferably, the acyl moiety of the monoacylglycerol is n-decanoyl, n-dodecanoyl, n-tetradecanoyl, n-hexadecanoyl, n-octadecanoyl, cis-octadec-9-enoyl (oleyl), cis,cis-9,12-octadecadienoyl (linoleyl) or cis,cis,cis-9,12,15-octadecatrienoyl (linolenyl). Most preferably, the monoacylglycerol is 1-n-decanoyl-glycerol or 1-n-octadecanoyl-glycerol.

The monoacylglycerol may be protected by one or more protecting groups during the preparation of the compounds of the present invention. Examples of suitable protecting groups, together with methods for their attachment and removal are described in Greene and Wuts, "Greene's Protective Groups in Organic Synthesis", 4th Edition, publ. Wiley, 2006. A particularly preferred protecting group is benzyl.

In order to prepare the compounds of the present invention, the monoacylglycerol may be present as an activated derivative. In this specification the term "activated derivative", when applied to a monoacylglycerol, means a derivative in which one or more (preferably only one) hydroxyl group of the monoacylglycerol has been converted to a leaving group. Examples of suitable leaving groups include halogen, acyloxy (where acyl is defined and exemplified above) and alkyl- or arylsulfonyloxy (for example benzenesulfonyloxy or p-toluenesulfonyloxy). A preferred leaving group is halogen, particularly chlorine.

Source of Amino- or N-Acylamino Monosaccharide Moiety

The source of the amino- or N-acylamino monosaccharide moiety in the compounds of the present invention is not especially critical, provided that it contains one or more amino- or N-acylamino monosaccharide moieties.

In the source of the amino- or N-acylamino monosaccharide moiety, the degree of acylation of the amino monosaccharide moiety may vary from 0 (ie no amino groups are acylated) to 1 (ie all amino groups are acylated). Preferably, preferably, the degree of acylation of the amino monosaccharide moiety ranges from 0.05 to 0.8.

The hydroxyl groups and/or amino groups of the amino- or N-acylamino monosaccharide moiety may be protected by one or more protecting groups during the preparation of the compounds of the present invention. Examples of suitable protecting groups, together with methods for their attachment and removal are described in Greene and Wuts, "Greene's Protective Groups in Organic Synthesis", 4th Edition, publ. Wiley, 2006. A particularly preferred protecting group is acetyl.

In order to prepare the compounds of the present invention, the source of the amino- or N-acylamino monosaccharide moiety may be present as an activated derivative. In this specification the term "activated derivative", when applied to the source of the amino- or N-acylamino monosaccharide moiety, means a derivative in which one or more (preferably only one) hydroxyl group of the source of the amino- or N-acylamino monosaccharide moiety has been converted to a leaving group. Examples of suitable leaving groups include halogen, acyloxy (where acyl is defined and exemplified above) and alkyl- or arylsulfonyloxy (for example benzenesulfonyloxy, p-toluenesulfonyloxy). A preferred leaving group is halogen, particularly chlorine.

When the reaction is carried out using an enzyme, the one or more amino- or N-acylamino monosaccharide moieties are attached to the remainder of the source molecule via a glycosidic bond, which is hydrolysed by the enzyme during the course of the transfer.

In one embodiment, it is preferred that the source of amino- or N-acylamino monosaccharide is a higher amino- or N-acylamino saccharide (ie a di-, oligo- or polysaccharide) comprising more than one amino- or N-acylamino monosaccharide moiety joined together by glycoside bonds, the enzyme acting to hydrolyse one or more glycoside bonds in the higher amino- or N-acylamino saccharide and transfer the amino- or N-acylamino monosaccharide moiety to the monoglyceride. In this regard, the amino- or N-acylamino monosaccharide moieties which form the higher amino- or N-acylamino saccharide may be the same or different, and may each independently have the D- or IL-configuration.

The amino- or N-acylamino monosaccharide moieties which form the higher amino- or N-acylamino saccharide may each independently be aldose or ketose moieties, and may have the same or different numbers of carbon atoms. Suitably, each amino- or N-acylamino monosaccharide moiety may have 3 to 8, preferably 4 to 6, and more preferably 5 or 6, carbon atoms.

In another embodiment, the monosaccharide moieties which form the higher amino- or N-acylamino saccharide are hexose moieties. Preferably, the hexose moieties of such a higher saccharide include one or more amino- or N-acylamino glucose moieties (in particular, glucosamine or N-acetylglucosamine moieties). In one particularly preferred embodiment, all of the hexose moieties of such a higher saccharide are amino- or N-acylamino glucose moieties (in particular, glucosamine or N-acetylglucosamine moieties).

The amino- or N-acylamino monosaccharide moieties which form the amino- or N-acylamino higher saccharide are joined together by glycoside bonds. When the monosaccharide moieties are hexose moieties, the glycoside bonds may be 1-α,1'-α glycoside bonds, 1,2'-glycoside bonds (which may be 1-α-2' or 1-β-2' glycoside bonds), 1,3'-glycoside bonds (which may be 1-α-3' or 1-β-3'-glycoside bonds), 1,4'-glycoside bonds (which may be 1-α-4' or 1-β-4'-glycoside bonds), 1,6'-glycoside bonds (which may be 1-α-6' or 1-β-6'-glycoside bonds), or any combination thereof. Preferably, the glycoside bonds are 1,4'-glycoside bonds, particularly 1-β-4'-glycoside bonds.

In one embodiment, the higher amino- or N-acylamino saccharide comprises 2 amino- or N-acylamino monosaccharide units (ie is an amino- or N-acylamino disaccharide). The degree of acylation of such an amino- or N-acylamino disaccharide may vary from 0 (ie an aminodisaccharide wherein neither amino groups on any aminomonosaccharide moiety are acylated) to 1 (ie an N-acylaminodisaccharide in which both amino groups on all aminomonosaccharide moieties are acylated). Preferably, the degree of acylation of the amino disaccharide ranges from 0.05 to 0.95.

Examples of suitable amino- or N-acylamino disaccharides include chitobiose, which is a dimer of β-1,4-linked glucosamine units, or an N-acyl derivative thereof, especially N-acetylchitobiose. The degree of acetylation of the chitobiose may vary from 0 (ie neither amino group on any glucosamine moiety are acetylated) to 1 (ie both amino groups on all glucosamine moieties are acylated). In one embodiment the degree of acetylation is 0. In another embodiment the degree of acetylation is 1. In a further embodiment, the degree of acetylation of the chitobiose ranges from 0.05 to 0.95.

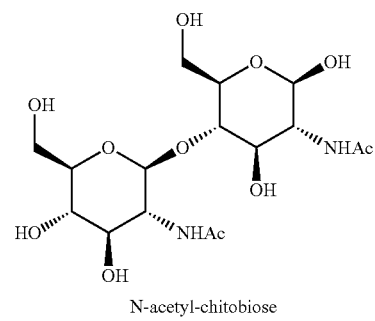

N-acetyl-chitobiose

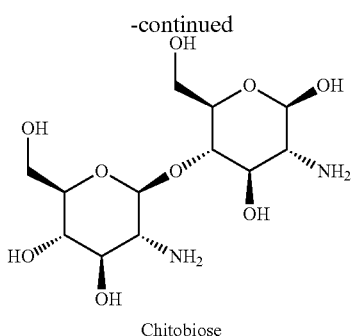

Chitobiose

In another embodiment, the higher amino- or N-acylamino saccharide comprises 3 to 10 monosaccharide units (ie is an amino- or N-acylamino oligosaccharide) or is an amino- or N-acylamino polysaccharide, comprising at least 10 higher amino- or N-acylamino monosaccharide units joined together by glycoside bonds. Typically such amino- or N-acylamino polysaccharides comprise at least 40, for example at least 100, such as at least 200, including at least 500, for example at least 1000, such as at least 5000, for example 10000, such as at least 50000, for example 100000, amino- or N-acylamino monosaccharide units.

In one embodiment, the amino- or N-acylamino polysaccharide comprises chitin. Chitin is a polysaccharide; it is synthesized from units of N-acetylglucosamine. These units form covalent β-1,4 glycosidic linkages (similar to the linkages between glucose units forming cellulose).

In another one embodiment, the amino- or N-acylamino polysaccharide comprises chitosan, which is a linear polysaccharide composed of randomly distributed β-(1-4)-linked D-glucosamine (deacetylated unit) and N-acetyl-D-glucosamine (acetylated unit).

Preferably the source of amino- or N-acylamino monosaccharide moiety is selected from chitosan, chitobiose, or an N-acyl derivative of any thereof, the acyl group having 1 to 6 carbon atoms. More preferably, the source of amino- or N-acylamino monosaccharide moiety is selected from chitosan or chitobiose, or an N-acetyl derivative of either thereof.

Monosaccharide Source

When the compounds of the present invention include an oligosaccharide chain wherein at least one of the monosaccharide moieties in the chain is an unsubstituted monosaccharide moiety, such compounds are generally formed by reacting either a monoacylglycerol (or an active derivative thereof) or an amino-substituted glycolipid (ie a compound of the present invention having one monosaccharide moiety fewer than the target compound), with an (unsubstituted) monosaccharide source to add this unsubstituted monosaccharide to the chain.

The source of monosaccharide moiety to be transferred according to the present invention is not especially critical, provided that it contains an unsubstituted monosaccharide moiety. When the compounds of the present invention are prepared by chemical synthesis, the source of the monosaccharide moiety may be a free monosaccharide, as described and exemplified above. However, when the compounds of the present invention are prepared by enzymatic synthesis, the monosaccharide moiety is attached to the remainder of the source molecule via a glycosidic bond, which is hydrolysed by the enzyme during the course of the transfer.

In particular, when the compounds of the present invention are prepared by enzymatic synthesis, it is preferred that the source of monosaccharide is a higher saccharide (ie a di-, oligo- or polysaccharide) comprising more than one monosaccharide moiety joined together by glycoside bonds, the enzyme acting to hydrolyse one or more glycoside bonds in the higher saccharide and transfer the monosaccharide to the acceptor molecule. In this embodiment, the monosaccharide moieties which form the higher saccharide may be the same or different, and may each independently have the D- or L-configuration.

In one embodiment, the monosaccharide moieties which form the higher saccharide may each independently be aldose or ketose moieties, and may have the same or different numbers of carbon atoms. Suitably, each monosaccharide moiety may have 3 to 8, preferably 4 to 6, and more preferably 5 or 6, carbon atoms.

In one embodiment, the monosaccharide moieties which form the higher saccharide are hexose moieties, examples of which include aldohexoses such as glucose, galactose, allose, altrose, mannose, gulose, idose and talose and ketohexoses such as fructose and sorbose. Preferably, the hexose moieties of such a higher saccharide include one or more glucose moieties. In one particularly preferred embodiment, all of the hexose moieties of such a higher saccharide are glucose moieties.

In another embodiment, the monosaccharide moieties which form the higher saccharide are pentose moieties such as ribose, arabinose, xylose or lyxose. Preferably, the pentose moieties of such a higher saccharide are arabinose or xylose moieties.

The monosaccharide moieties which form the higher saccharide are joined together by glycoside bonds. When the monosaccharide moieties are hexose moieties, the glycoside bonds may be 1-α,1'-α glycoside bonds, 1,2'-glycoside bonds (which may be 1-α-2' or 1'-β-2' glycoside bonds), 1,3'-glycoside bonds (which may be 1-α-3' or 1-β-3'-glycoside bonds), 1,4'-glycoside bonds (which may be 1-α-4' or 1-β-4'-glycoside bonds), 1,6'-glycoside bonds (which may be 1-α-6' or 1-β-6'-glycoside bonds), or any combination thereof.

In one embodiment, the higher saccharide comprises 2 monosaccharide units (ie is a disaccharide). Examples of suitable disaccharides include maltose, isomaltose, isomaltulose, lactose, sucrose, cellobiose, nigerose, kojibiose, trehalose and trehalulose.

In another embodiment, the higher saccharide comprises 3 to 10 monosaccharide units (ie is an oligosaccharide) in a chain, which may be branched or unbranched. Preferably, the oligosaccharide comprises 3 to 8, more preferably 3 to 6, monosaccharide units. Examples of suitable oligosaccharides include maltodextrin, maltotriose, maltotetraose, maltopentaose, maltohexaose, maltoheptaose, melezitose, cellotriose, cellotetraose, cellopentaose, cellohexaose and celloheptaose.

In another embodiment, the higher saccharide is a polysaccharide, comprising at least 10 monosaccharide units joined together by glycoside bonds. Typically such polysaccharides, comprise at least 40, for example at least 100, such as at least 200, including at least 500, for example at least 1000, such as at least 5000, for example 10000, such as at least 50000, for example 100000, monosaccharide units.

In some embodiments, the polysaccharide comprises from 10 to 500000 monosaccharide units. In other embodiments, the polysaccharide comprises from 100 to 1000 monosaccharide units. In other embodiments, the polysaccharide comprises from 1000 to 10000 monosaccharide units. In other embodiments, the polysaccharide comprises from 10000 to 100000 monosaccharide units. In some embodiments, the polysaccharide comprises from 40 to 3000, preferably 200 to 2500, monosaccharide units.

Examples of such polysaccharides include starch and derivatives thereof (such as cationic or anionic, oxidised or phosphated starch), amylose, amylopectin, glycogen, cellulose or a derivative thereof (such as carboxymethyl cellulose), alginic acid or a salt or derivative thereof, polydextrose, pectin, pullulan, carrageenan, locust bean gum and guar and derivatives thereof (such as cationic or anionic guar).

In one embodiment, the polysaccharide comprises starch. Starches are glucose is polymers in which glucopyranose units are bonded by a-linkages. It is made up of a mixture of amylose and amylopectin. Amylose consists of a linear chain of several hundred glucose molecules linked together by 1,4'-α-glycoside linkages. In contrast amylopectin is a branched molecule made of several thousand glucose units, the main chain comprising 1,4'-α-glycoside linkages but having 1,6'-α-glycoside branches approximately every 25 glucose units.

In one embodiment, the polysaccharide comprises glycogen. Glycogen is a polysaccharide that is found in animals and is composed of a branched chain of glucose residues.

In one embodiment, the polysaccharide comprises cellulose. Cellulose is a polymer formed from several thousand glucose units bonded together by 1,4'-β-glycoside linkages.

Preferred sources of the monosaccharide moiety include sucrose and maltose.

Enzymatic Synthesis

In one aspect, the compounds of the present invention may be prepared using a transglycosidase enzyme, the enzyme catalysing the hydrolysis of a glycosidic bond in the source of amino- or N-acylamino monosaccharide moiety and the transfer of this moiety to the monoglyceride acceptor molecule.

Thus, in one embodiment, there is provided a method of preparing a compound of the present invention, comprising treating a monoacylglycerol, the acyl moiety thereof being a saturated or unsaturated acyl group having 3 to 40 carbon atoms, with a source of amino- or N-acylamino monosaccharide moiety and a transglycosidase enzyme.

In this specification the term 'transglycosidase enzyme' is intended to cover any enzyme capable of transferring a monosaccharide moiety (as defined and exemplified above, either in its broadest aspect or a preferred aspect, particularly although not exclusively an unsubstituted monosaccharide moiety and/or an amino- or N-acylamino monosaccharide moiety) from one molecule to another. The term 'transglycosidase' is used when the monosaccharide moiety is a glucose moiety.

In one embodiment, the transglycosidase enzyme is an aminoglycosyltransferase enzyme. In this specification the term "aminoglycosyltransferase enzyme" means an enzyme capable of catalysing the transfer of an amino- or N-acylamino monosaccharide moiety (as defined and exemplified above) from a suitable amino- or N-acylamino monosaccharide source (as defined and exemplified above) to an acceptor molecule, preferably a monoglyceride (as defined and exemplified above).

Suitably, the transglycosidase activity of the enzyme may comprise at least 0.5%, preferably at least 2%, more preferably at least 5% of the total activity of the enzyme. The remaining activity of the enzyme may, for example, substantially comprise hydrolytic activity, wherein the acceptor substrate is water.

In the present invention, the percentage transglycosidase activity (in particular aminoglycosyltransferase activity) of the enzyme may be calculated by measuring the molar proportions of free monosaccharide (specifically, amino- or N-acylamino monosaccharide) and the proportion of compounds of the present invention wherein the monosaccharide (specifically, amino- or N-acylamino monosaccharide) is bound to a monoglyceride, following conclusion of the reaction. The free monosaccharides (specifically, amino- or N-acylamino monosaccharides) result from enzymatic hydrolysis of the source molecule, whereas compounds of the present invention result from enzymatic transfer of the monosaccharide (specifically, amino- or N-acylamino monosaccharide) from the source molecule to the monoglyceride.

Typical transglycosidase enzyme-catalysed reactions follow the reaction Scheme 1 below.

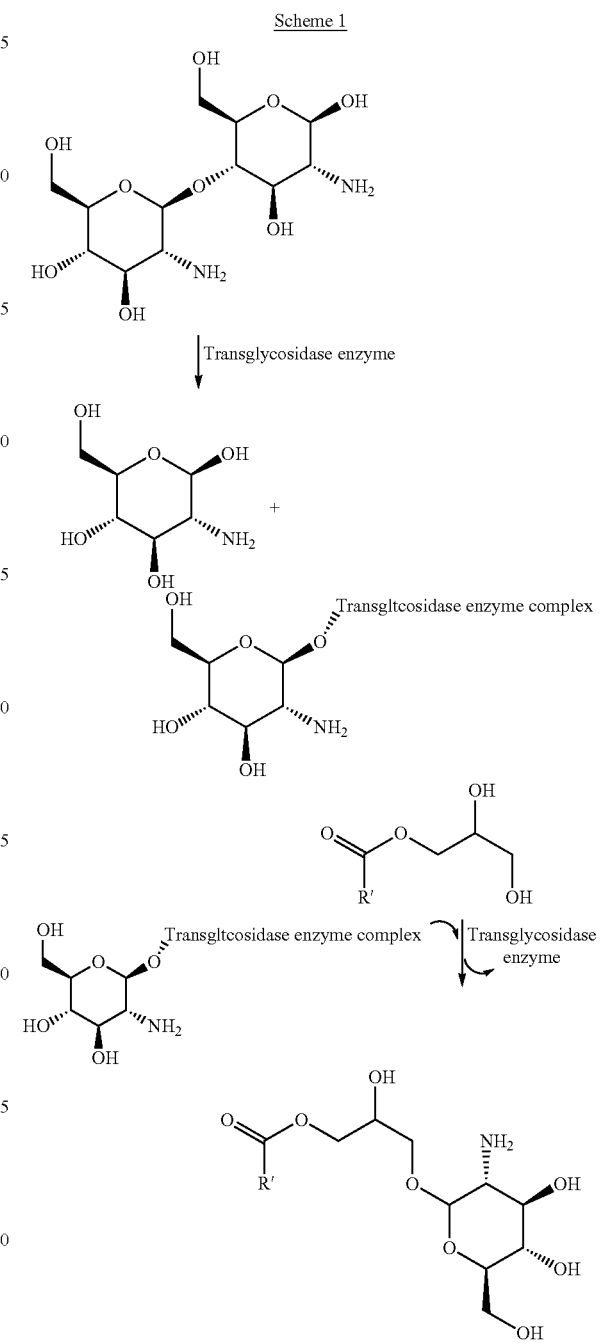

In Scheme 1, R' is the hydrocarbyl part of an acyl group, as defined and exemplified above.

Suitably, the transglycosidase enzyme is classified in Enzyme Classification (E.C.) 3.2.1.21 or E.C 3.2.1.74.

In one embodiment, the transglycosidase enzyme is a β-glucosidase enzyme. Beta-glucosidase is a glucosidase enzyme that acts upon β1->4 bonds linking two glucose moieties such as the disaccharide cellobiose. It catalyzes the hydrolysis of terminal non-reducing residues in beta-D-glucosides with release of glucose.

Surprisingly, it has been found according to the present invention that the β-glucosidase enzymes used in the present invention also exhibit transglycosidase activity (as described above), in particular aminoglycosyltransferase activity. This would not have been expected as the principal activity of β-glucosidase enzymes is hydrolytic activity.

Typically, the transglycosidase activity of the β-glucosidase enzyme is at least 0.5%, preferably at least 2%, more preferably at least 5% of the total activity of the enzyme.

Amino Acid Sequences

Amino acid sequences of transglycosidase enzymes capable of transferring an amino- or N-acylamino monosaccharide moiety to a lipid, as defined herein, particularly transglycosidase enzymes having the amino acid sequence of SEQ ID No. 1 defined below, or has at least 50%, preferably at least 55%, such as at least 60%, at least 65%, at least 70%, at least 75%, at least 80%, at least 85%, at least 90%, at least 95%, at least 96%, at least 97%, at least 98% or at least 99%, sequence identity therewith, may be used in the present invention.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The protein used in the present invention may be used in conjunction with other proteins, particularly other enzymes, for example amylases, proteases or lipases. Thus the present invention may also employ a composition comprising a combination of enzymes wherein the combination comprises the transglycosidase enzyme used in the present invention and another enzyme, which may be, for example, another transglycosidase enzyme as described herein. This aspect is discussed in a later section.

Sequence Identity/Sequence Homology/Variants/Homologues/Derivatives

The present invention also encompasses the use of polypeptides having a degree of sequence identity or sequence homology with amino acid sequence(s) defined herein or with a polypeptide having the specific properties defined herein. The present invention encompasses, in particular, peptides having a degree of sequence identity with SEQ ID No. 1, defined below, or homologues thereof. Here, the term "homologue" means an entity having sequence identity with the subject amino acid sequences or the subject nucleotide sequences. Here, the term "homology" can be equated with "sequence identity".

The homologous amino acid sequence and/or nucleotide sequence should provide and/or encode a polypeptide which retains the functional activity and/or enhances the activity of the transglycosidase enzyme.

In the present context, a homologous sequence is taken to include an amino acid sequence which may be at least 60%, for example at least 65%, at least 70%, at least 75%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score),
ii) assignment of a penalty score each time an existing gap is extended with an extra position (extension penalty score),
iii) assignment of high scores upon alignment of identical amino acids, and
iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools are available from the ExPASy Proteomics server. Another example of software that can perform sequence alignment is BLAST (Basic Local Alignment Search Tool), which is available from the webpage of National Center for Biotechnology Information and which was firstly described in Altschul et al. *J. Mol. Biol.* (1990) 215; 403-410. A further example of software that can perform sequence alignment is BLAST2 which was firstly described in Tatusova and Madden, *FEMS Microbiol. Lett.* (1999) 174, 247-250.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage under tools—sequence analysis—ClustalW2.

Thus, the present invention also encompasses the use of variants, homologues and derivatives of any amino acid sequence of a protein as defined herein, particularly those of SEQ ID No. 1, defined below.

The sequences, particularly SEQ ID No. 1, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine, and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as), norleucine ornithine (hereinafter referred to as (O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxylamino acids (Serine, Threonine), large amino acids (Phenylalanine and Tryptophan) and small amino acids (Glycine, Alanine).

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, La-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-conservative substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino add residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al. (1992), Horwell D C. (1995).

Purified

In one aspect, preferably the sequence used in the present invention is in a purified form. The term "purified" means that a given component is present at a high level. The component is desirably the predominant active component present in a composition.

Amount/Concentration

The amount of transglycosidase required in the glycosylation method of the present invention is not particularly limited.

In one embodiment, the enzymatic transfer methods of the present invention require an effective amount of the transglycosidase enzyme. In this specification the term 'effective amount' means an amount of transglycosidase enzyme capable of causing a measurable quantity of amino- or N-acylamino monosaccharide moiety to be transferred to the monoglyceride molecule.

The amount of amino- or N-acylamino monosaccharide moiety transferred to the lipid acceptor molecule may be measured using Liquid Chromatography-Mass Spectrometry (LC-MS).

For example, the reduction in the amount of amino- or N-acylamino monosaccharide source or the increase in the amount of the product in the reaction mixture may be measured at different time points during the reaction.

The transglycosidase enzyme may be present in any concentration to enable it to perform the above required function of transferring an amino- or N-acylamino monosaccharide moiety to a monoglyceride.

In one embodiment, the transglycosidase is present in a concentration of 1-1000 units of transglycosidase activity (U), preferably 2-400 U and most preferably 5-200 Upper gram of the monoglyceride acceptor.

In one embodiment, the transglycosidase is present in a concentration of 0.00033-0.33 g, preferably 0.00067-0.13 g and most preferably 0.0017-0.067 g per gram of the monoglyceride acceptor.

When the transglycosidase enzyme is a β-glucosidase enzyme, the transglycosidase activity can be measured by reference to its β-glucosidase activity. One unit of β-glucosidase activity is defined as the amount of enzyme which produces 1 µmol p-nitrophenol from p-nitrophenyl β-D-glucopyranoside per minute under the conditions of the assay (pH 4.8 and 50° C.). The required transglycosidase activity can then be calculated based on the proportions of transglycosidase and hydrolytic activity (as a % of the total activity), referred to above.

In one embodiment, the transglycosidase enzyme is of fungal origin or has at least 50%, preferably at least 55%, such as at least 60%, at least 65%, at least 70%, at least 75%, at least 80%, at least 85%, at least 90%, at least 95%, at least 96%, at least 97%, at least 98% or at least 99%, sequence identity with a transglycosidase enzyme of fungal origin.

Preferably, the transglycosidase enzyme originates from a *Trichoderma* species or has at least 50%, preferably at least 55%, such as at least 60%, at least 65%, at least 70%, at least 75%, at least 80%, at least 85%, at least 90%, at least 95%, at least 96%, at least 97%, at least 98% or at least 99%, sequence identity with a transglycosidase enzyme originating from a *Trichoderma* species.

In a particularly preferred embodiment, the transglycosidase enzyme is *Trichoderma reesei* (SEQ ID No 1) or has at least 50%, preferably at least 55%, such as at least 60%, at least 65%, at least 70%, at least 75%, at least 80%, at least 85%, at least 90%, at least 95%, at least 96%, at least 97%, at least 98% or at least 99%, sequence identity therewith.

The enzyme having the sequence of SEQ ID No 1 corresponds to amino acids 32-744 of the mature enzyme having the sequence of SEQ ID No 2, the first 31 amino acids constituting a signal peptide. Accordingly, reference in this specification to SEQ ID No 1 can also be understood to mean also to a peptide having amino acids 32-744 of SEQ ID No 2, or a peptide having at least 60%, at least 65%, at least 70%, at least 75%, at least 80%, at least 85%, at least 90%, at least 95%, at least 96%, at least 97%, at least 98% or at least 99%, sequence identity therewith.

Enzyme Combinations

The transglycosidase enzyme (in particular, the aminoglycosyltransferase enzyme) may be used according to the present invention in combination with one or more further active agents. Such combinations may offer advantages, including synergy, when used together in a composition, in particular a foodstuff.

In particular, the transglycosidase enzyme (in particular, the aminoglycosyltransferase enzyme) may be used according to the present invention in combination with one or more further enzymes as active agents. Such combinations may offer advantages, including synergy, when used together in a composition, in particular a foodstuff.

In one embodiment, the further enzyme is another transglycosidase enzyme (in particular, a further aminoglycosyltransferase enzyme), so that two (or more) different transglycosidase (particularly aminoglycosyltransferase) enzymes are used in combination. Without wishing to be bound by theory, it is envisaged that one aminoglycosyltransferase may catalyse the transfer of one amino- or N-acylamino monosaccharide moiety to a monoglyceride acceptor and another transglycosidase (for example, aminoglycosyltransferase) may catalyse the transfer to the amino- or N-acylamino monosaccharide moiety on the resultant amino- or N-acylaminoglycosylmonoglyceride thereby elongating the glucan chain on the monoglyceride.

In one embodiment, the further enzyme is a glycosidase (E.C. 3.2.1). Without wishing to be bound by theory, it is envisaged that combining a glycosidase with the transgiycosidase enzyme of the present invention may be particularly advantageous in that the glycosidase is capable of hydrolysing glycoside bonds of longer-chain higher saccharides to shorter-chain higher saccharides (especially di- and oligosaccharides), the monosaccharide moieties of which can then be more easily transferred to the monoglyceride or glycosylmonoglyceride acceptor than from such longer-chain higher saccharides. The glycosidase may be an α-glycosidase or a β-glycosidase. In particular, the glycosidase may comprise an amylase, such as α-amylase (E.C. 3.2.1.1) or β-amylase (EC. 3.2.1.2). Such amylase enzymes are capable of hydrolysing starch to shorter-chain oligosaccharides such as maltose: the glucose moiety can then be more easily transferred from maltose to a monoglyceride or glycosylmonoglyceride than from the original starch molecule.

In one embodiment, the further enzyme is a hexosyltransferase (EC. 2.4.1). Without wishing to be bound by theory, it is envisaged that combining a hexosyltransferase with the transglycosidase enzyme of the present invention may be particularly advantageous in that the hexosyltransferase is capable of transferring monosaccharide moieties (such as amino- or N-acylamino monosaccharide moieties) from compounds on which the transglycosidase enzyme of the present invention is generally inactive to form other compounds, such as mono- or higher saccharides (especially di- and oligosaccharides) on which the transglycosidase enzyme of the present invention can act to transfer the monosaccharide moieties to the a monoglyceride or glycosylmonoglyceride. In addition, without wishing to be bound by theory, it is envisaged that glucosyltransferases and other hexosyltransferases could transfer one or more monosaccharide moieties to the monosaccharide moiety or moieties already present on or previously transferred to the monoglyceride or glycosylmonoglyceride by the transglycosidase of the present invention, thereby elongating the glucan chain on the monoglyceride.

In another embodiment, the further enzyme is a carboxylic ester hydrolase (E.C.3.1.1). Without wishing to be bound by theory, it is envisaged that combining a carboxylic ester hydrolase with the transglycosidase enzyme of the present invention may be particularly advantageous in that the carboxylic ester hydrolase is capable of partially hydrolysing a triglyceride (which lacks the necessary free OH group to accept a monosaccharide moiety) into a monoglyceride which can act as an acceptor molecule in the present invention. In particular, the carboxylic ester hydrolase may comprise a carboxylesterase (E.C. 3.1.1.1).

Examples of further classes of enzymes suitable for combination with the transglycosidase in the present invention include oxidases (E.C.1.1.3) and O-acyltransferases (particularly those classed in E.C. 2.3.1.43).

Chemical Synthesis—General

The compounds of formula (I) may be made according to general Schemes 2 and 3 below.

Scheme 2

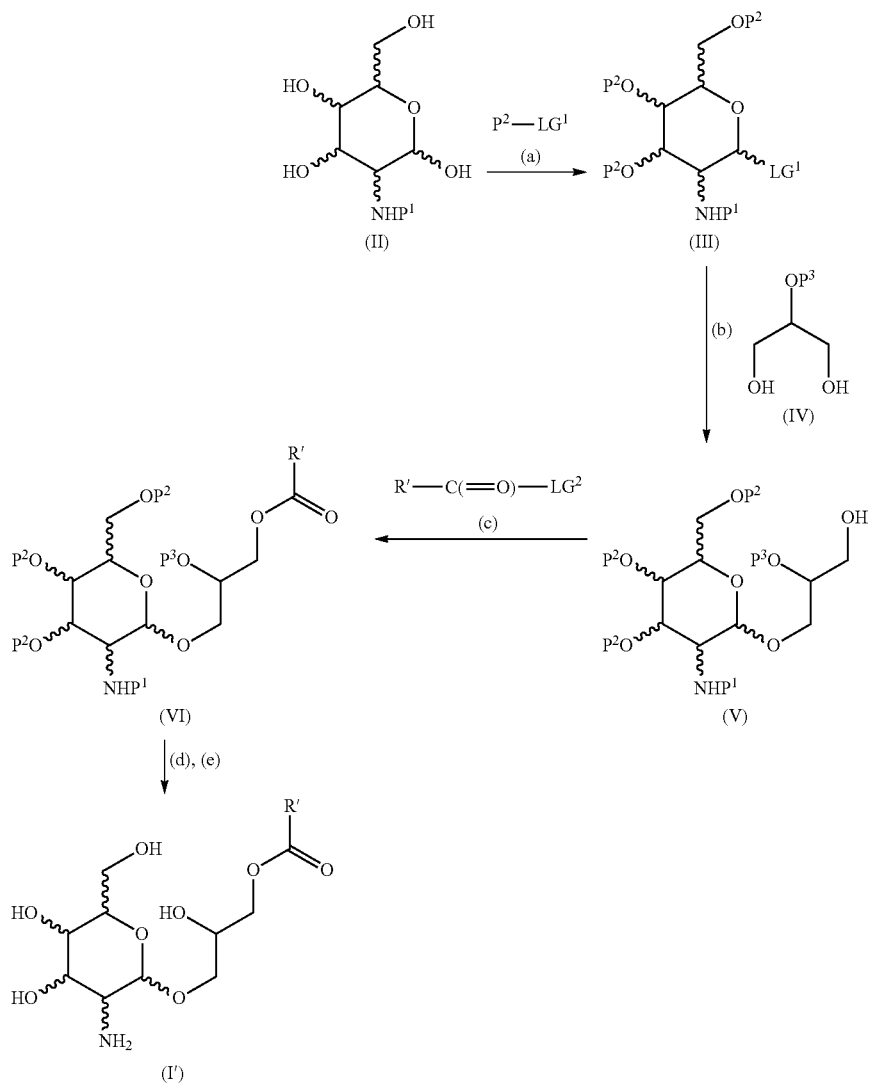

In Scheme 2, compounds of formula (I') are compounds of formula (I) having only a single amino monosaccharide moiety bonded to the glycerol unit.

R' is the hydrocarbyl part of an acyl group (as defined and exemplified above);

$P^1$ is an amino-protecting group, examples of which are described in Greene & Wuts (2006), referred to above, especially an acyl group having 1-6 carbon atoms, particularly acetyl;

$P^2$ is a hydroxy-protecting group, especially an acyl group having 1-6 carbon atoms, particularly acetyl;

$P^3$ is a hydroxy-protecting group, examples of which are described in Greene & Wuts (2006), referred to above, especially benzyl;

$LG^1$ is a leaving group, for example halogen, alkoxy group having 1-6 carbon atoms, or an acyloxy group having 1-6 carbon atoms, especially halogen, particularly chlorine; and $LG^2$ is a leaving group, for example halogen, alkoxy group having 1-6 carbon atoms, or an is acyloxy group having 1-6 carbon atoms, especially halogen, particularly chlorine.

Step (a): Protection of the non-anomeric hydroxyl groups with simultaneous conversion of the anomeric hydroxyl group into a leaving group, can be carried out by standard methods, for example as described in "Best Synthetic Methods: Carbohydrates" Elsevier Science Ltd. 2003, pp 69-80. Typically, the reagent $P^2$-$LG^1$ is an acid chloride, especially acetyl chloride.

Step (b): Coupling of the protected amino sugar of formula (III) with a protected glycerol of formula (IV) may be carried out in the presence of an acid, which may be a Brønsted acid (such as a strong mineral acid) or a Lewis acid such as $ZnCl_2$.

Step (c): Acylation of the compound of formula (V) to provide the protected compound of formula (VI) can be accomplished with an acylating agent of formula R—C(=O)-$LG^2$, such as an acid chloride or acid anhydride.

Steps (d) and (e): Deprotection of the compound of formula (VI) may be carried out using standard methods, such as those described in Greene & Wuts (2006), referred to above. When $P^1$ is acyl, the deprotection may be carried out such that only the groups $P^2$ are removed to provide an N-acylamino compound of formula (I). A typical deprotecting agent when $P^2$ is acyl is hydrazine. A typical deprotecting agent when $P^3$ is benzyl is hydrogen in the presence of a metal catalyst, such as palladium.

Scheme 3

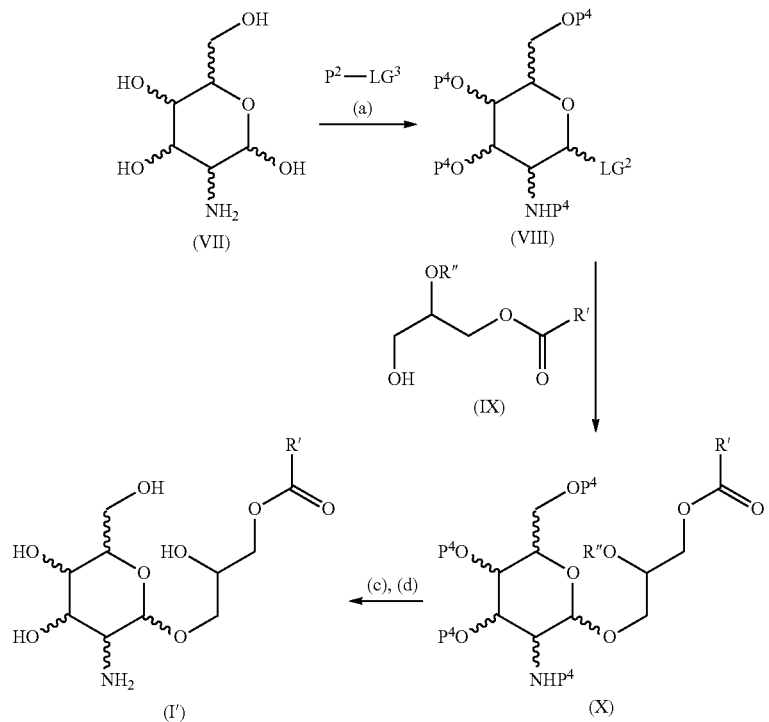

In Scheme 3:
R' is as defined in Scheme 2;
R'' is H or P³, wherein P³ is as defined in Scheme 2;
P⁴ is a group capable of protecting both a hydroxy group and an amino group, examples of which are described in Greene & Wuts (2006), referred to above, especially acetyl; and
LG³ is a leaving group, for example halogen or an acyloxy group having 1-6 carbon atoms, particularly acetyloxy.
Step (a): Protection of the non-anomeric hydroxyl groups and the amino group of the amino sugar of formula (VII) with simultaneous conversion of the anomeric hydroxyl group into a leaving group, can be carried out by standard methods, for example as described in "Best Synthetic Methods: Carbohydrates" Elsevier Science Ltd. 2003, pp 69-80. Typically, the reagent P⁴-LG³ is an acid anhydride, especially acetic anhydride.
Step (b): Coupling of the protected amino sugar of formula (VIII) with a protected monoacylglycerol of formula (IX) may be carried out in the presence of an acid catalyst, such as a strong mineral acid. A typical catalyst is $H_2SO_4$ supported on silica.
Steps (c) and (d): Deprotection of the compound of formula (X) may be carried out using standard methods, such described in Greene & Wuts (2006), referred to above. A typical deprotecting agent when P⁴ is acyl is hydrazine. A typical deprotecting agent when P³ is benzyl is hydrogen in the presence of a metal catalyst, such as palladium.

INDUSTRIAL APPLICATIONS

The compounds of the present invention find use in a number of applications, particularly as emulsifiers and/or surfactants, and as antimicrobial agents.
In particular, the compounds of the present invention are biodegradable, natural cationic surfactants which find applications as detergents in household care. They also exhibit antimicrobial properties against a range of bacteria (both gram negative and gram positive) as well as moulds and yeast. They have surface active antimicrobial effect in thermoplastics including extruded products and film, and find application as antimicrobial and emulsification facilitator in personal care products including over-the-counter (OTC) creams.

Foodstuff

The compounds of the present invention may be incorporated into, and/or be used in the preparation of, a foodstuff or feedstuff. The term "foodstuff" as used herein means a substance which is suitable for human and/or animal consumption. The term "feedstuff" as used herein specifically refers to substances suitable for animal consumption.
Suitably, the term "foodstuff" as used herein may mean a foodstuff in a form which is ready for consumption. Alternatively or in addition, however, the term foodstuff as used herein may mean one or more food materials which are used in the preparation of a foodstuff.
The foodstuff may be in the form of a solution or as a solid—depending on the use and/or the mode of application and/or the mode of administration.
When used as—or in the preparation of—a food—such as functional food—the compounds of the present invention may be used in conjunction with one or more of: a nutritionally acceptable carrier, a nutritionally acceptable diluent, a nutritionally acceptable excipient, a nutritionally acceptable adjuvant, a nutritionally active ingredient.
In a preferred aspect the present invention provides a foodstuff (as defined above) including the compounds of the present invention wherein the foodstuff is selected from one or more of the following: eggs, egg-based products, including but not limited to mayonnaise, salad dressings, sauces, ice creams, egg powder, modified egg yolk and to products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

Suitably the foodstuff in accordance with the present invention may be a "fine food", including cakes, pastry, confectionery, chocolates, fudge and the like.

In one aspect the foodstuff in accordance with the present invention may be a dough product or a baked product, such as bread, a fried product, a snack, cakes, pies, brownies, cookies, noodles, snack items such as crackers, graham crackers, pretzels, potato chips, tortillas, nachos and pasta.

In a further aspect, the foodstuff in accordance with the present invention may be a plant derived food product such as flours, pre-mixes, oils, fats, cocoa butter, coffee whitener, salad dressings, margarine, spreads, peanut butter, shortenings, ice cream, cooking oils.

In another aspect, the foodstuff in accordance with the present invention may be a dairy product, including butter, milk, cream, cheese such as natural, processed, and imitation cheeses in a variety of forms (including shredded, block, slices or grated), cream cheese, ice cream, frozen desserts, yoghurt, yoghurt drinks, butter fat, anhydrous milk fat, other dairy products. The enzyme according to the present invention may improve fat stability in dairy products.

In another aspect, the foodstuff in accordance with the present invention may be a food product containing animal derived ingredients, such as processed meat products, cocking oils, shortenings.

In a further aspect, the foodstuff in accordance with the present invention may be a beverage, a fruit, mixed fruit, a vegetable, a marinade or wine.

In one aspect, the foodstuff in accordance with the present invention is a plant derived oil (i.e. a vegetable oil), such as olive oil, sunflower oil, peanut oil or rapeseed oil.

The compounds of the present invention may be generated in situ in a foodstuff or feedstuff.

Therefore, in a further aspect the invention provides a method for in situ generation of a compound of the present invention in a foodstuff or feedstuff composition, the composition comprising the following components:
(i) a monoacylglycerol (as defined and exemplified above) or an activated derivative thereof;
(ii) a source of amino- or N-acylamino monosaccharide moiety (as defined and exemplified above), or an activated derivative thereof;
(iii) if required, a source of unsubstituted monosaccharide moiety (as defined and exemplified above) or an activated derivative thereof; and
(iv) if required, a suitable catalyst or activating agent; the method comprising adding to the composition any of components (i) and (ii) that are not already present in the composition and, if required (iii) and/or (iv) that are not already present in the composition, and allowing the components to react.

Cleaning and Detergent Compositions

The compounds of the present invention may form a component of a cleaning and/or detergent composition. In general, cleaning and detergent compositions are well described in the art and reference is made to WO 96/34946; WO 97/07202; and WO 95/30011 for further description of suitable cleaning and detergent compositions.

The compounds of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In one embodiment the laundry composition of the present invention may comprise a compound of the present invention in combination with one or more enzymes, such as a protease, an amylase, a glucoamylase, a maltogenic amylase, a non-maltogenic amylase, a lipase, a cutinase, a carbohydrase, a cellulase, a pectinase, a mannanase, an arabinase, a galactanase, a xylanase, an oxidase, a laccase, and/or a peroxidase, and/or combinations thereof. In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115. Suitable commercially available protease enzymes include Alcalase®, Savinase®, Liquanase®, Ovozyme®, Polarzyme®, Esperase®, Everlase®, and Kannase® (Novozymes, formerly Novo Nordisk A/S); Excellase™, Maxatase®, Maxacal™, Maxapem™, Properase®, Properase L®, Purafect®, Purafect L®, PuraFast™, OxP™, FN2™, and FN3™ (Genencor—a division of Danisco A/S).

Lipases: The enzyme may be a lipase (EC 3.1.1) capable of hydrolysing carboxylic ester bonds to release carboxylate. Examples of lipases include but are not limited to triacylglycerol lipase (EC 3.1.1.3), galactolipase (EC 3.1.1.26), phospholipase A1 (EC 3.1.1.32, phospholipase A2 (EC 3.1.1.4) and lipoprotein lipase A2 (EC 3.1.1.34). Suitable lipases include those of bacterial or fungal origin. Chemically modified or protein engineered mutants are included. Examples of useful lipases include, but are not limited to, lipases from *Humicola* (synonym *Thermomyces*), e.g. *H. lanuginosa* (*T. lanuginosus*) (see, e.g., EP 258068 and EP 305216) and *H. insolens* (see, e.g., WO 96/13580); a *Pseudomonas* lipase (e.g., from *P. alcaligenes* or *P. pseudoalcaligenes*; see, e.g., EP 218 272), *P. cepacia* (see, e.g., EP 331 376), *P. stutzeri* (see, e.g., GB 1,372,034), *P. fluorescens, Pseudomonas* sp. strain SD 705 (see, e.g., WO 95/06720 and WO 96/27002), *P. wisconsinensis* (see, e.g., WO 96/12012); a *Bacillus* lipase (e.g., from *B. subtilis*; see, e.g., Dartois et al. (1993)), *B. stearothermophilus* (see, e.g., JP 64/744992), or *B. pumilus* (see, e.g., WO 91/16422). Additional lipase variants contemplated for use in the formulations include those described, for example, in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipex®, Lipolase® and Lipolase® Ultra (Novozymes, formerly Novo Nordisk A/S).

Polyesterases: Suitable polyesterases include, but are not limited to, those described in WO 01/34899 (Genencor) and WO 01/14629 (Genencor), and can be included in any combination with other enzymes discussed herein.

Amylases: The compositions can comprise amylases such as α-amylases (EC 3.2.1.1), G4-forming amylases (EC 3.2.1.60), β-amylases (EC 3.2.1.2) and γ-amylases (EC 3.2.1.3). These can include amylases of bacterial or fungal origin, chemically modified or protein engineered mutants are included. Commercially available amylases, such as, but not limited to, Duramyl®, Termamyl™, Fungamyl® and BAN™ (Novozymes, formerly Novo Nordisk A/S), Rapidase®, and Purastar® (Danisco USA, Inc.), LIQUEZYME™, NATALASET™, SUPRAMYL™, STAINZYME™, FUNGAMYL and BAN™ (Novozymes A/S), RAPIDASE™, PURASTAR™ and PURASTAROXAM™ (from Danisco USA Inc.), GRINDAMYL™ PowerFresh, POWERFlex™ and GRINDAMYL PowerSoft (from Danisco A/S)

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME® (Novozymes A/S).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophile* and *Fusarium oxysporum* disclosed in U.S. Pat. Nos. 4,435,307; 5,648,263; 5,691,178; 5,776,757; and WO 89/09259, for example. Exemplary cellulases contemplated for use are those having color care benefit for the textile. Examples of such cellulases are cellulases described in EP 0495257; EP531372; WO 99/25846 (Genencor International, Inc.), WO 96/34108 (Genencor International, Inc.), WO 96/11262; WO 96/29397; and WO 98/08940, for example. Other examples are cellulase variants, such as those described in WO 94/07998; WO 98/12307; WO 95/24471; WO 99/01544; EP 531 315; U.S. Pat. Nos. 5,457,046; 5,686,593; and 5,763,254. Commercially available cellulases include Celluzyme®, Carezyme® and Endolase® (Novozymes, formerly Novo Nordisk A/S); Clazinase™ and Puradax® HA (Genencor); and KAC-500(B)™ (Kao Corporation).

Examples of commercially available mannanses include MANNAWAY™ (Novozymes, Denmark) and MannaStar™ (Genencor).

The compounds of the present invention may be included in a detergent composition by adding separate additives containing one or more enzymes, or by adding a combined additive comprising all of these enzymes. A compound of the invention, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly (ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP-A-238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition may also comprises one or more further surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or other N-acyl or N-alkyl derivatives of glucosamine.

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly (vinyl alcohol), poly (vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system which may comprise a hydrogen peroxide source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions the compound of the invention, may be added in an amount corresponding 0.5 to 25 g of the compound per liter of wash liquor, preferably 0.75 to 10 g of the compound per liter of wash liquor, in particular 1 to 5 g of the compound per liter of wash liquor.

In Situ Use in Laundry Compositions

The compounds of the present invention may be generated in situ in a laundry composition.

Therefore, in a further aspect the invention provides a method for in situ generation of a compound of the present invention in a laundry composition, the composition comprising the following components:
(i) a monoacylglycerol (as defined and exemplified above) or an activated derivative thereof;
(ii) a source of amino- or N-acylamino monosaccharide moiety (as defined and exemplified above), or an activated derivative thereof;
(iii) if required, a source of unsubstituted monosaccharide moiety (as defined and exemplified above) or an activated derivative thereof; and
(iv) if required, a suitable catalyst or activating agent;
the method comprising adding to the composition any of components (i) and (ii) that are not already present in the composition and, if required (iii) and/or (iv) that are not already present in the composition, and allowing the components to react.

In the above method, the monoacylglycerol and the source of amino- or N-acylamino monosaccharide moiety, or activated derivatives of either thereof, may be present as an initial component of the laundry composition. Alternatively, if no or insufficient monoacylglycerol or source of amino- or N-acylamino monosaccharide moiety (or activated derivatives of either thereof) is initially present, these components can be added to the composition.

The source of unsubstituted monosaccharide moiety (as defined and exemplified above) or an activated derivative thereof is required in order to generate in situ compounds of the present invention in which the first group is an oligosaccharide chain including unsubstituted monosaccharides. It may be present as an initial component of the laundry composition. Alternatively, if no or insufficient unsubstituted monosaccharide source is initially present, this component can be added to the composition.

If required, a catalyst (particularly an enzyme, especially a transglycosidase enzyme) may be present. It may be present as an initial component of the laundry composition. Alternatively, if no or insufficient catalyst is initially present, this component can be added to the composition.

The laundry composition may further comprise a lipase (E.C. 3.1.1).

The laundry composition may further comprise a stain, which may be a lipid (in particular, a triglyceride and/or a diglyceride and/or a monoglyceride). The stain may be on a surface, for example a fabric. The laundry composition of the present invention may therefore comprise a surface for example a fabric.

In one embodiment a laundry composition comprises a transglycosidase enzyme as defined herein, an amino- or N-acylamino monosaccharide source and a stain comprising monoglycerides. The amino- or N-acylamino monosaccharide moiety is transferred by the transglycosidase enzyme to the monoglyceride and a compound of the present invention is produced.

In one embodiment the stain comprises a triglyceride and the laundry composition further comprises a lipase. Hydrolysis of the triglyceride by the lipase provides a source of monoglycerides. An amino- or N-acylamino monosaccharide moiety is transferred by the transglycosidase enzyme to the monoglyceride to form a compound of the present invention.

Converting a triglyceride, diglyceride or a monoglyceride into a compound of the present invention may help remove a stain comprising a lipid from a fabric.

BRIEF DESCRIPTION OF THE FIGURES

FIG. 6 shows SEQ ID No. 1 (sequence used);

FIG. 7 shows SEQ ID No. 2 (mature sequence);

EXAMPLES

Example 1

Figure 1:
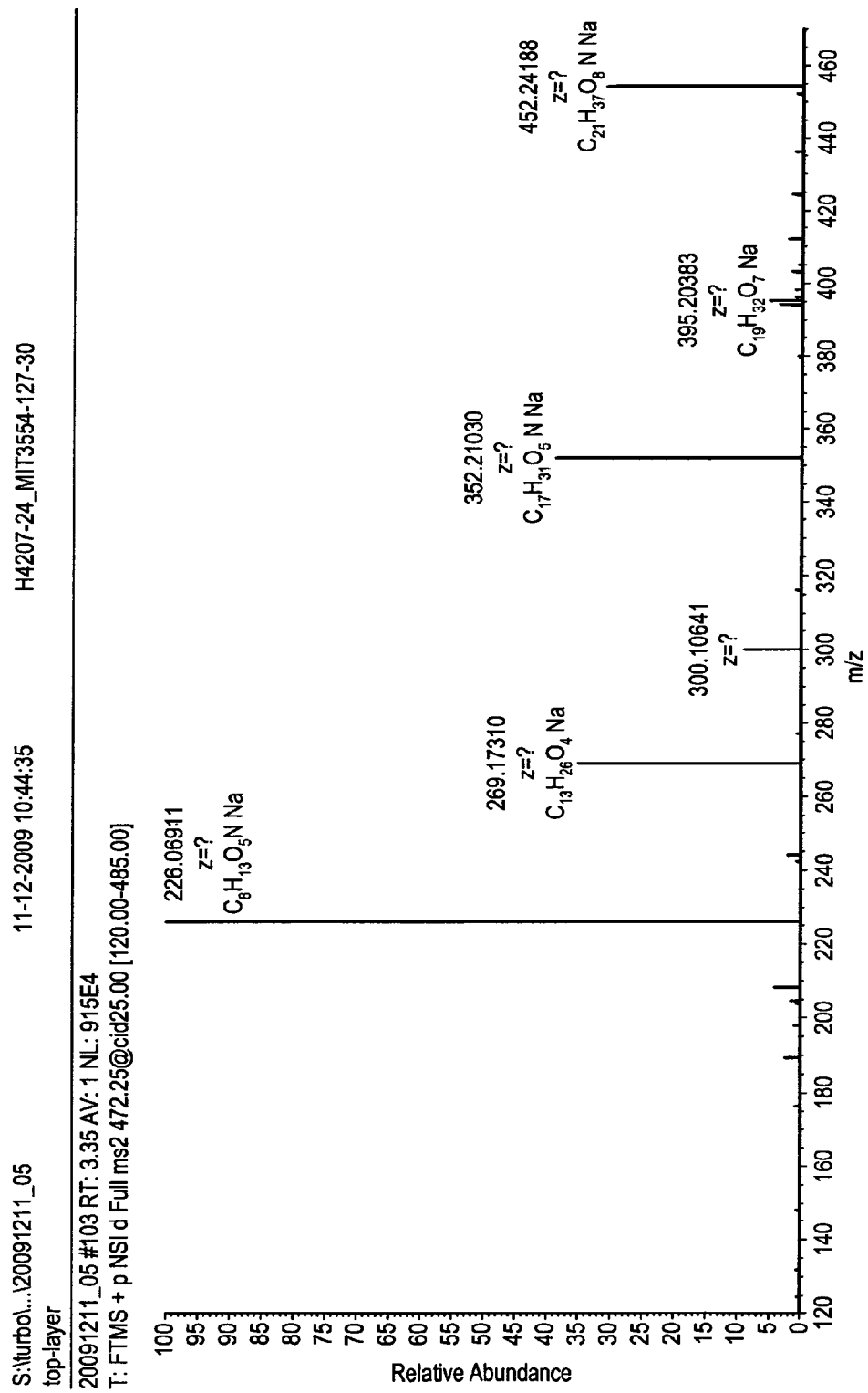
FIG. 1 is an MS$^2$-spectrum m/z 472.25, 1-O-(2-(acetylamino)-2-deoxy-β-D-glucopyranosyl)-3-n-decanoylglycerol (Compound 2), Na-adduct.
Figure 2:
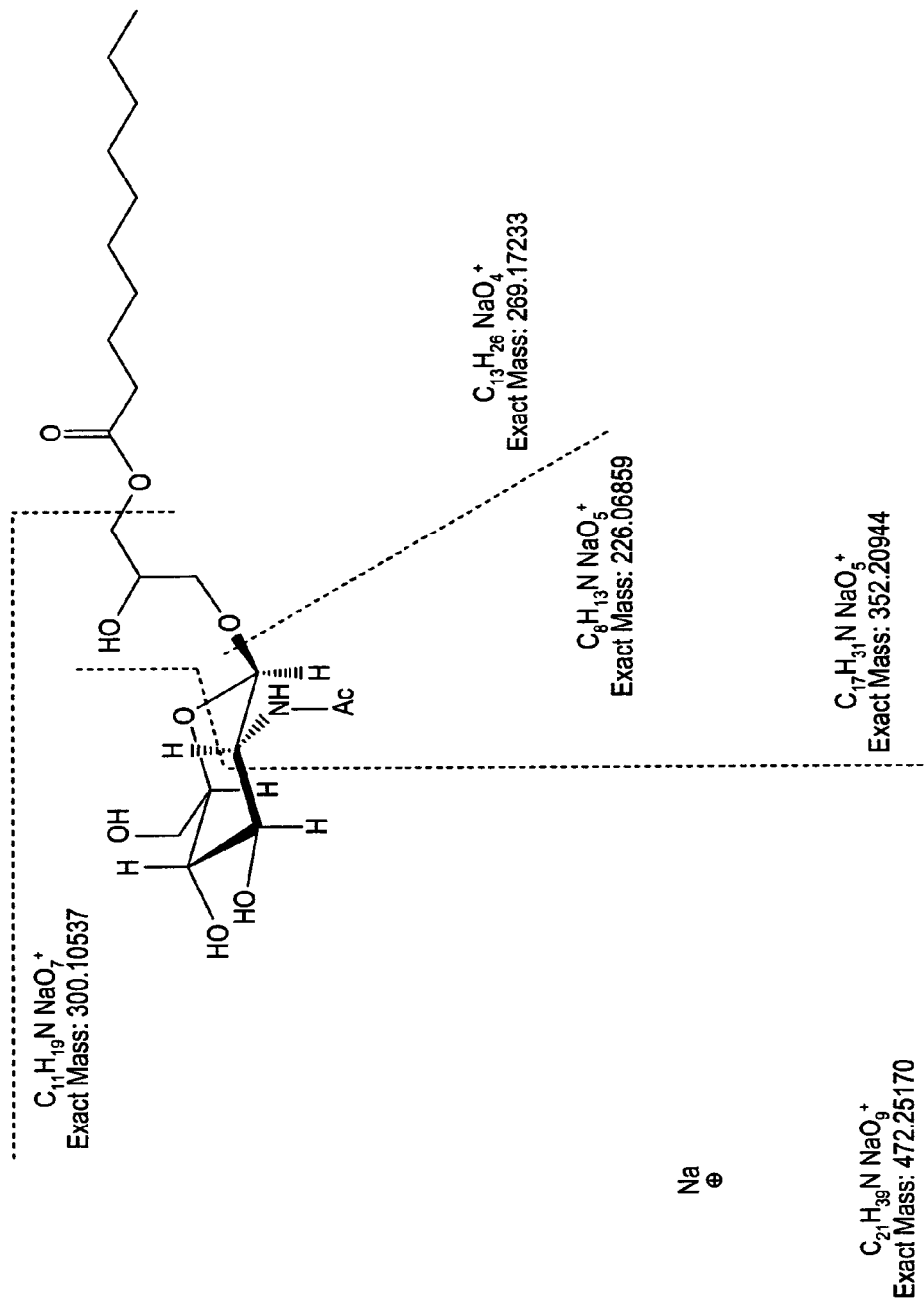
FIG. 2 assigns the fragments to the MS$^2$-spectrum of FIG. 1.
Figure 3:
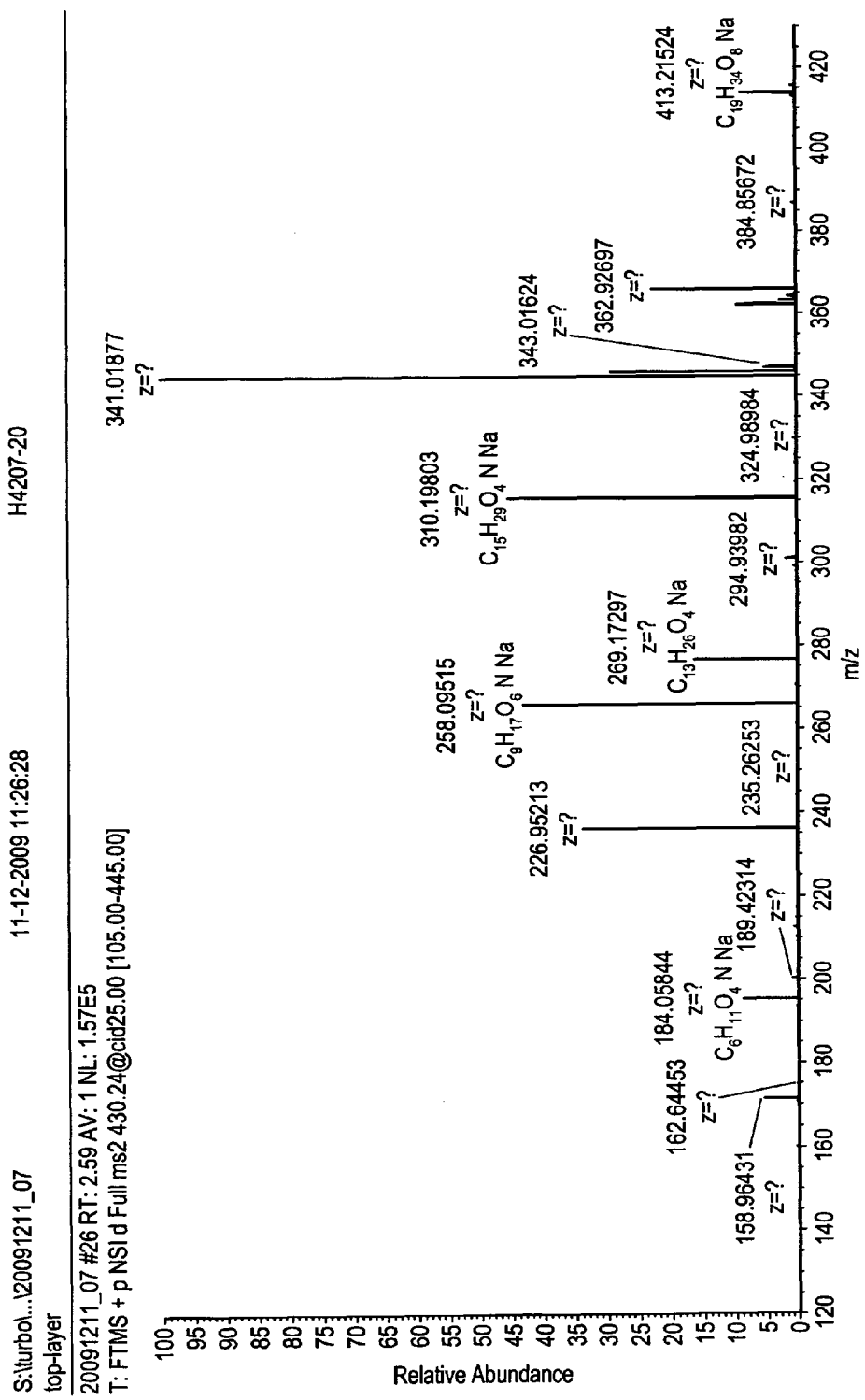
FIG. 3 is an MS$^2$-spectrum of m/z 430.24 1-O-(2-amino-2-deoxy-β-D-glucopyranosyl)-3-n-decanoylglycerol (Compound 1), Na-adduct)
Figure 4:
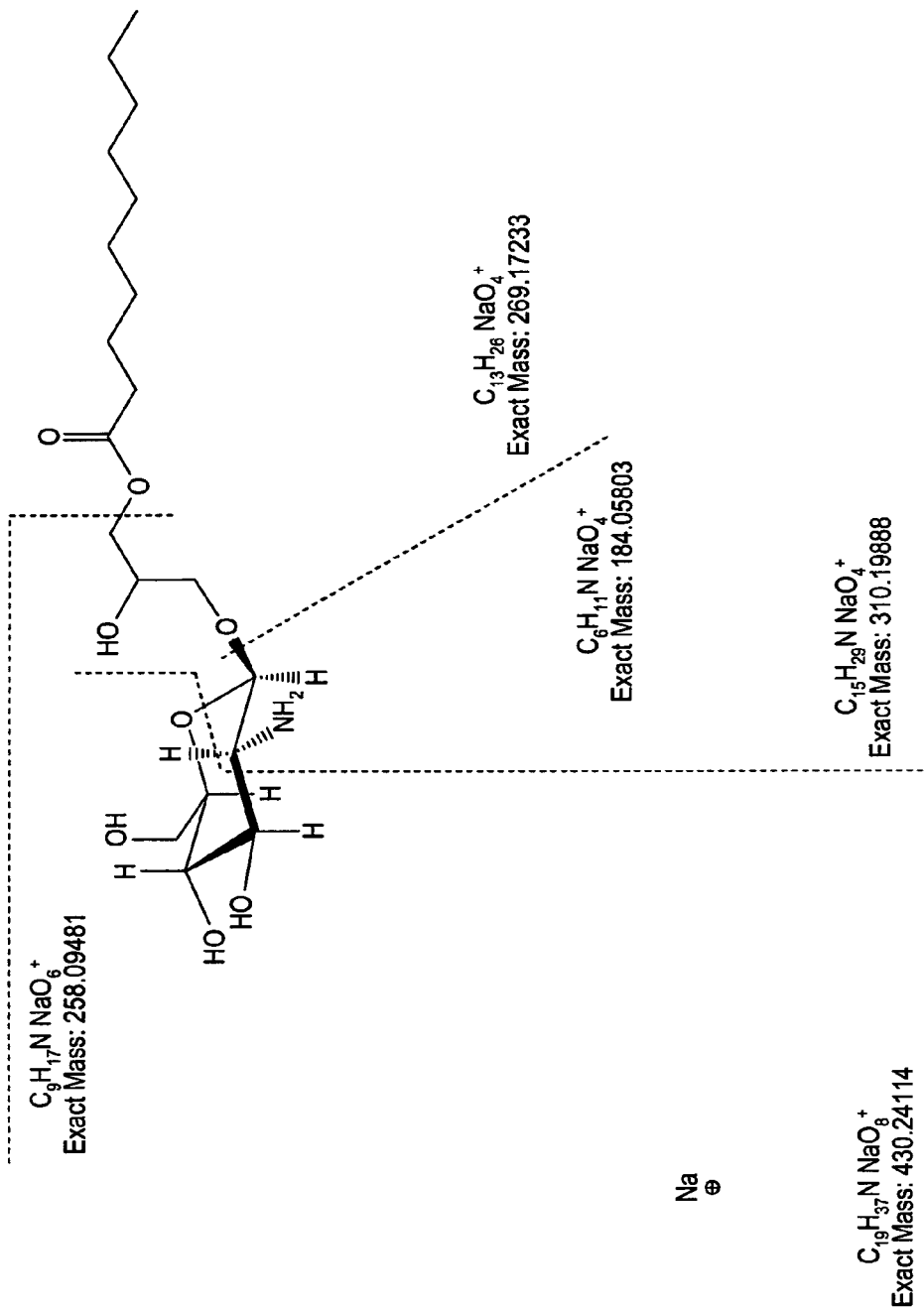
FIG. 4 assigns the fragments to the MS$^2$-spectrum of FIG. 3.
Figure 5:
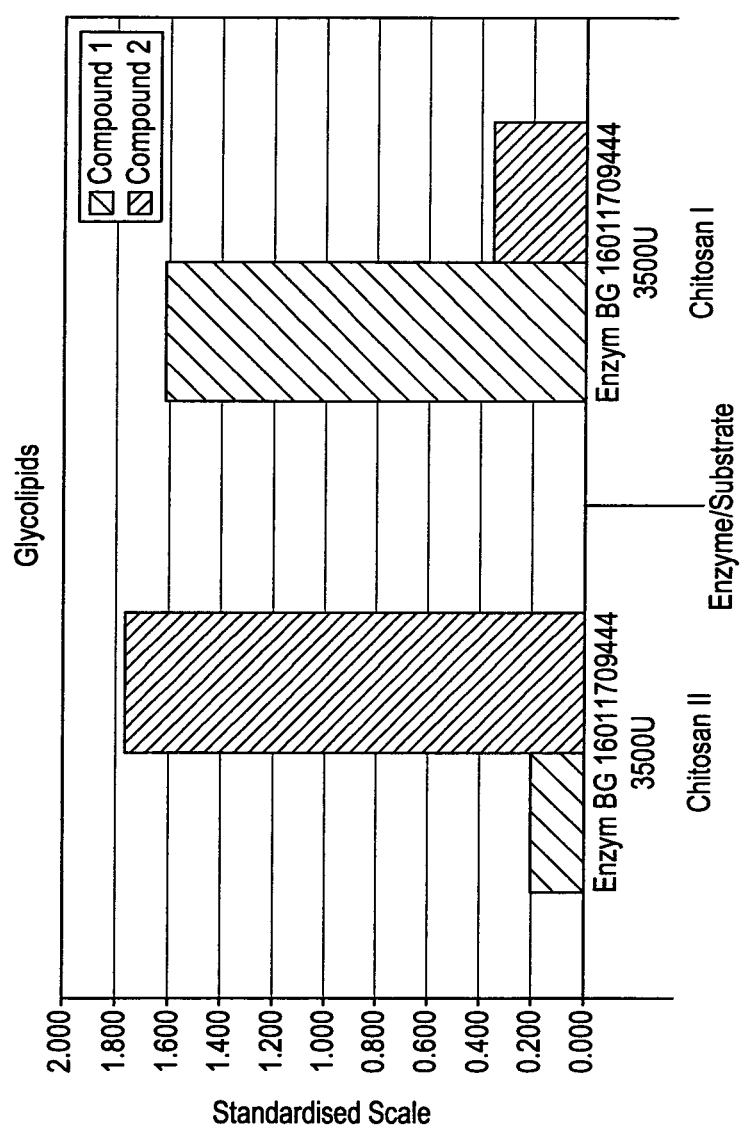
FIG. 5 shows a schematic representation of the HPLC/MS results shown in Table 3.
Figure 8:
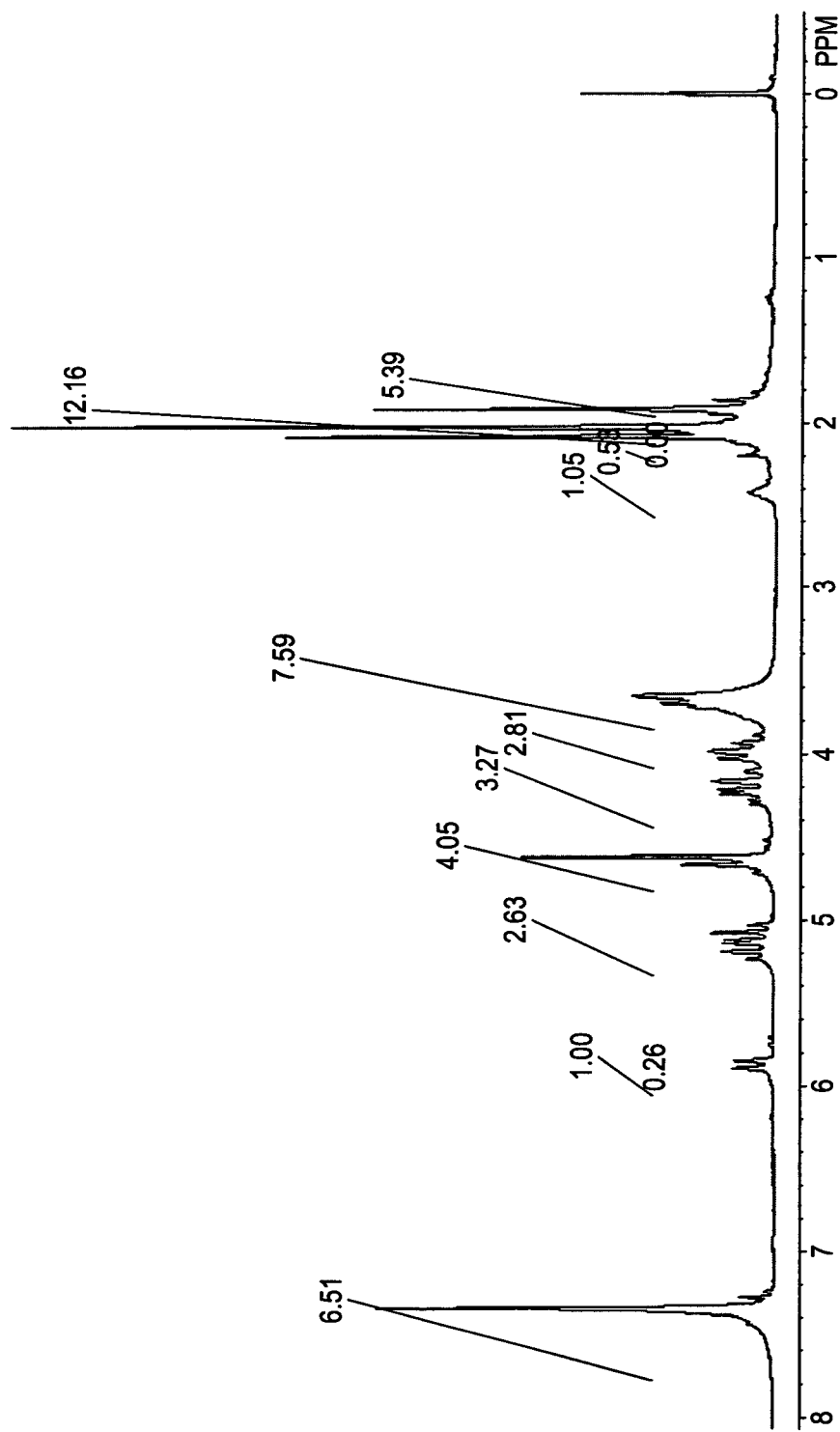
FIG. 8 is a $^1$H NMR spectrum of Intermediate 2.
Figure 9:
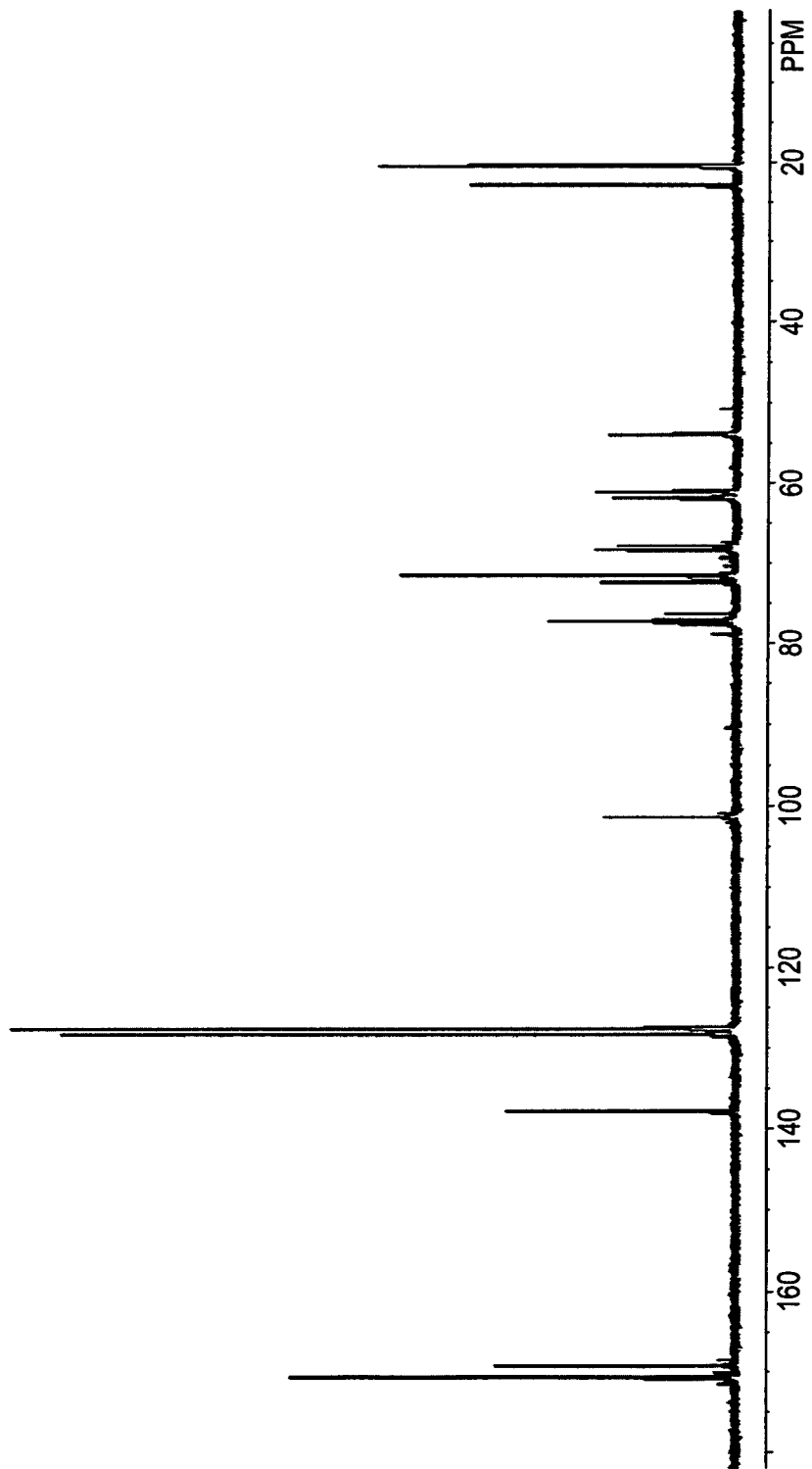
FIG. 9 is a $^{13}$C NMR spectrum of Intermediate 2.
Figure 10:
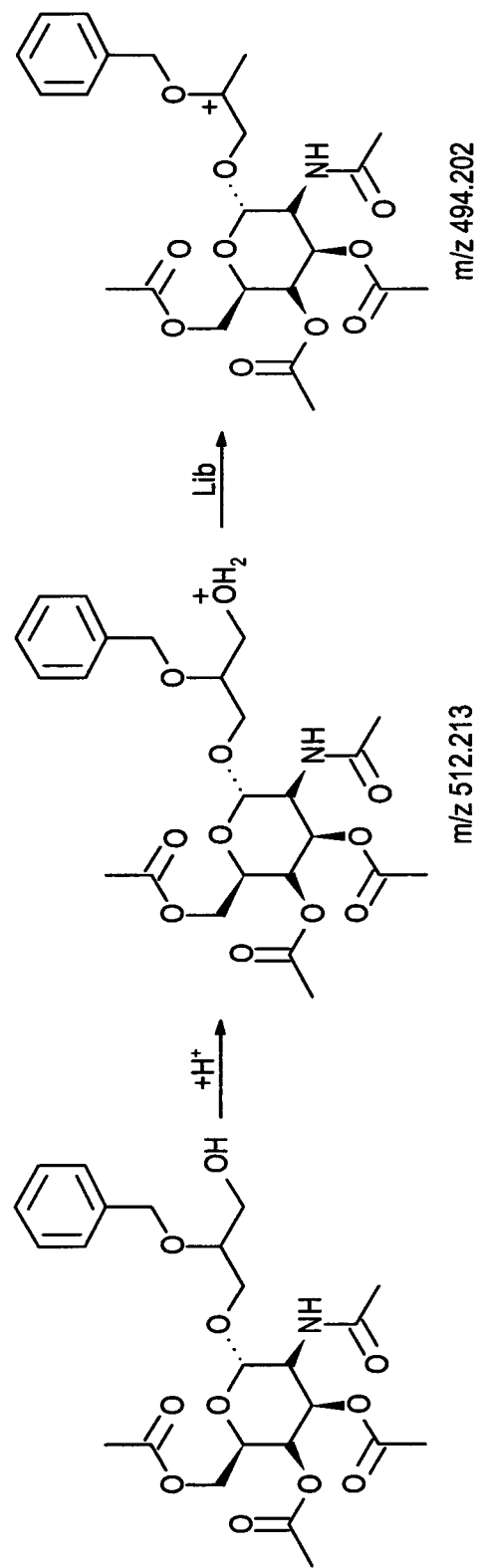
FIG. 10 assigns the fragments to the MS$^2$-spectrum of FIG. 14.
Figure 11:
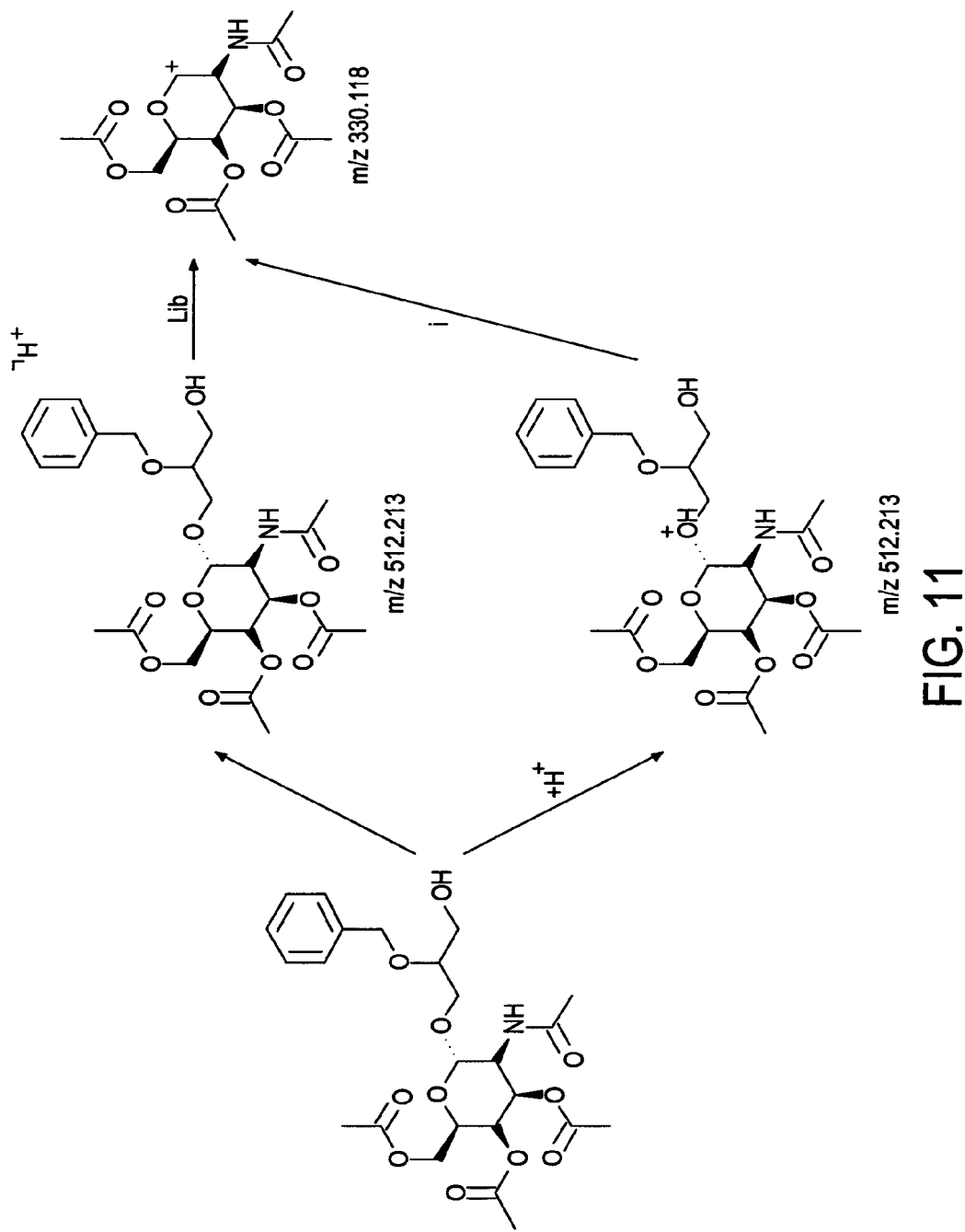
FIG. 11 is a further explanation of the fragments of the MS$^2$-spectrum of FIG. 14.
Figure 12:
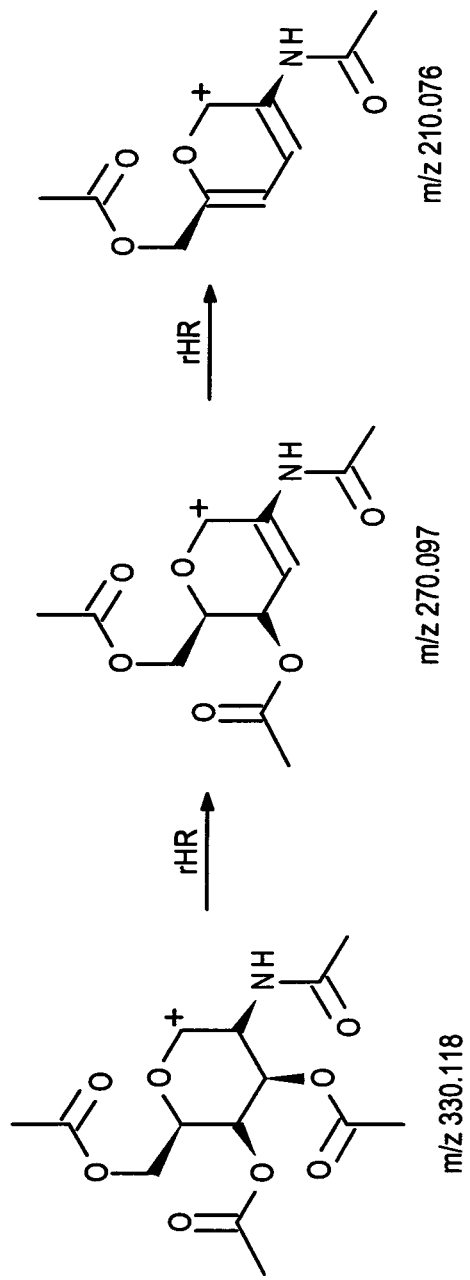
FIG. 12 assigns the fragments to the MS and MS$^3$-spectra of FIGS. 13 and 15.
Figure 13:
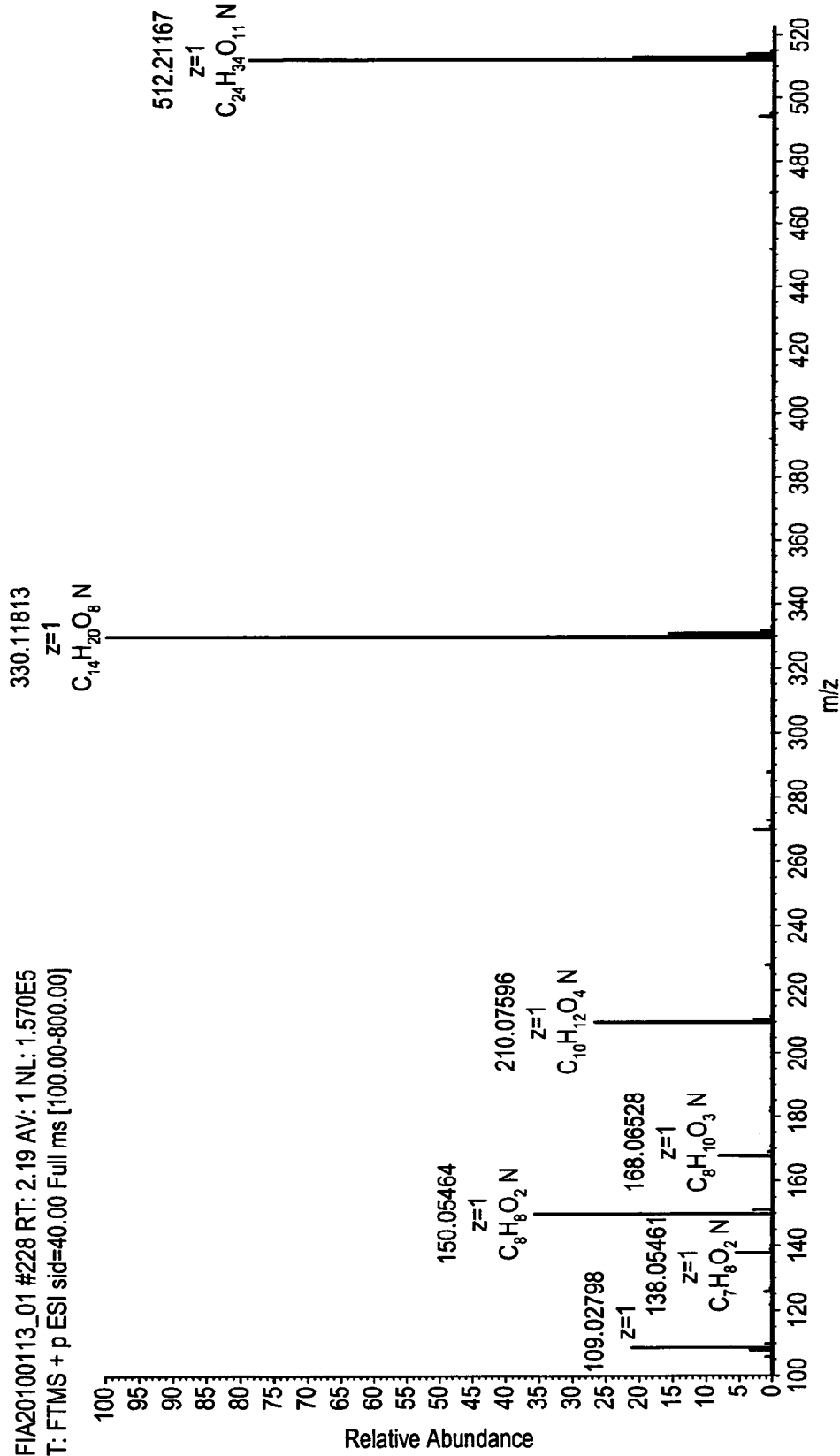
FIG. 13 is an MS spectrum of Intermediate 2.
Figure 14:
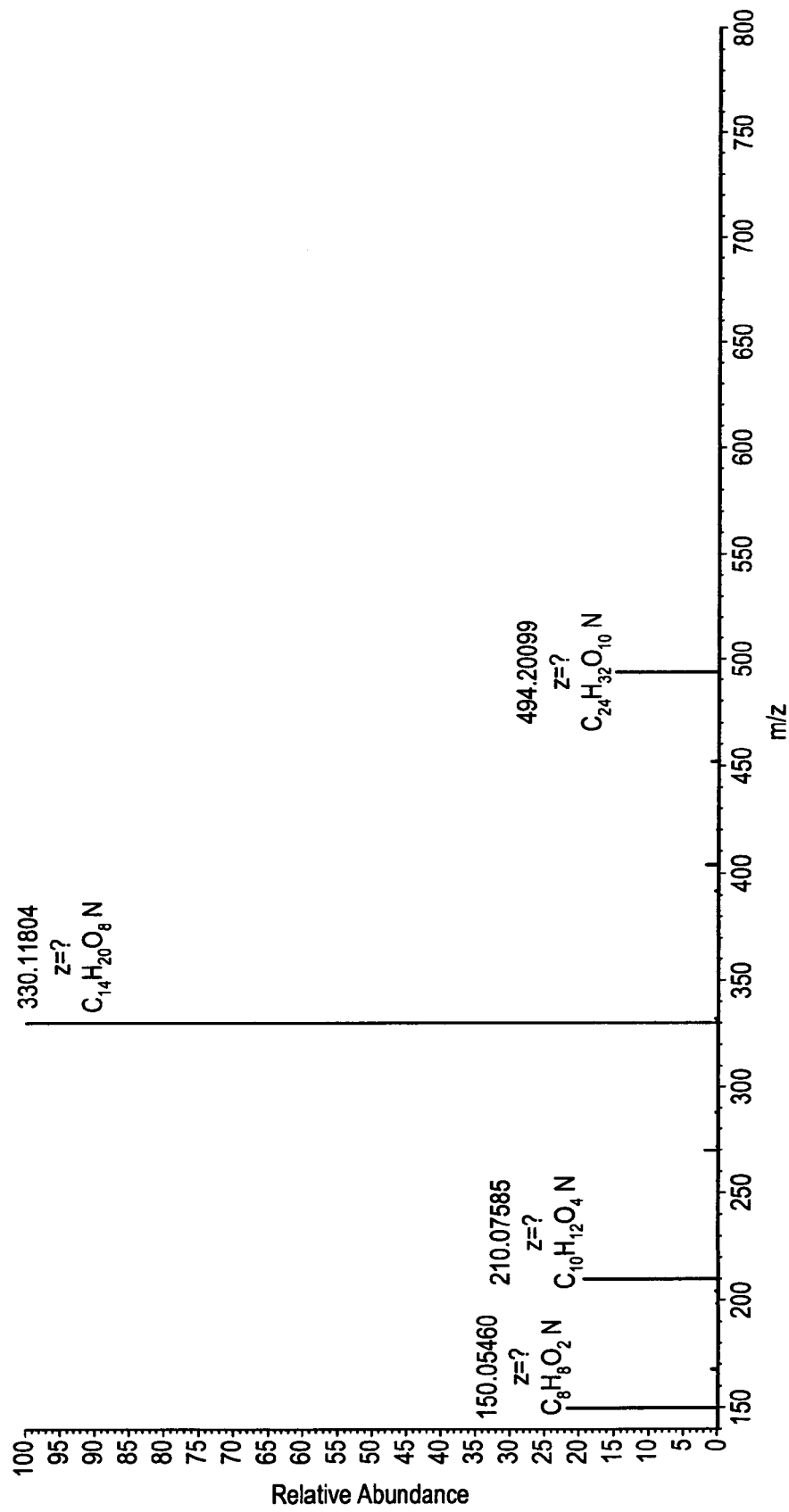
FIG. 14 is an MS$^2$ spectrum of Intermediate 2.
Figure 15:
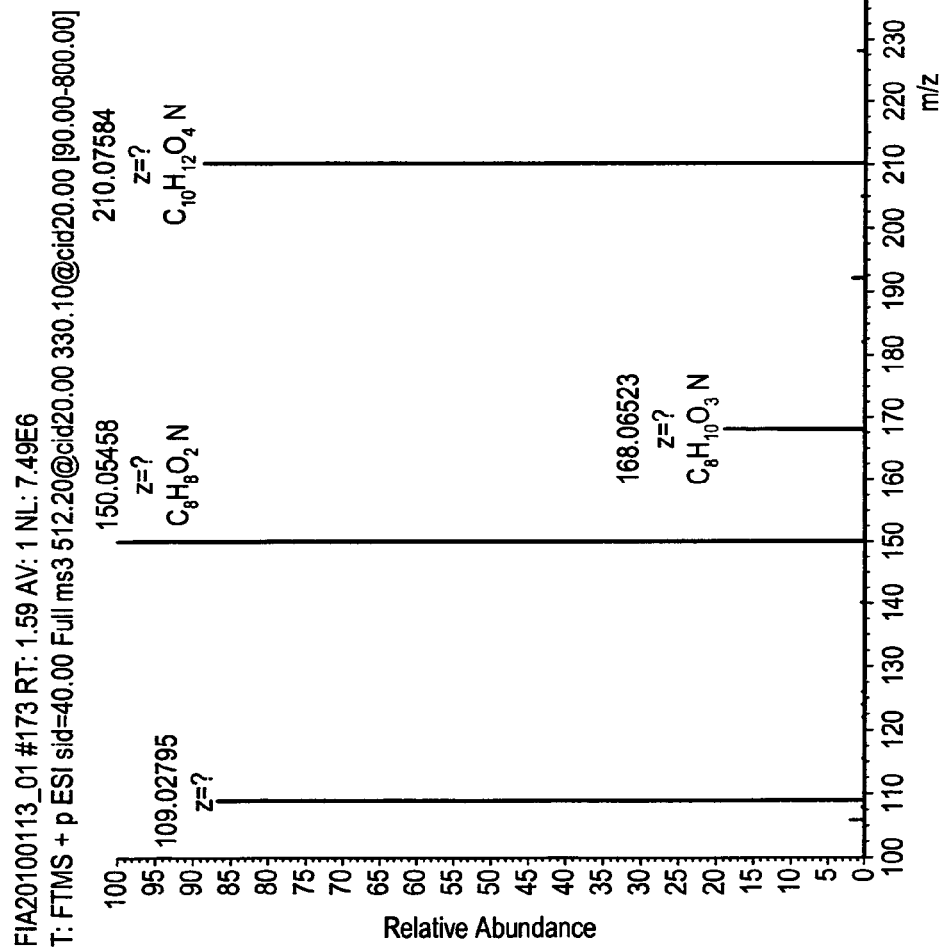
FIG. 15 is an MS$^3$ spectrum of Intermediate 2.

In Vitro Preparation of Chitobiose as Substrate for Glycosyl Transferase Reactions Chitobiose substrate was prepared from a sample of low molecular weight chitosan having low degree of acetylation and molecular weight. The procedure is described in Roncal et al. *Carbohydrate Res.*, 342, 2750-2756 (2007).

The following substrate was used: Chitosan I: Chitoclear™ 1979, from Primex.

TABLE 1

Chitosan samples for hydrolytic treatment with pepsin

| Chitosan sample | Molar Weight [kD] | Degree of acetylation [%] |
|---|---|---|
| Chitosan I | 48 | 3 |

A 50 mM sodium acetate buffer (pH 4.5) was firstly prepared by dissolving 4.10 g sodium acetate in 1000 mL demineralised water and adjusting with 1% aqueous acetic acid solution to pH 4.5.

Chitosan solution: 5% of the selected chitosan was dissolved in the above 50 mM sodium acetate buffer (pH 4.5).

5 g chitosan was added to 95 g buffer and heated to 80° C. in a round bottom glass flask. The chitosan dissolves to a slight viscous light orange liquid. The solution is cooled to 40° C. and added 0.05 gram pepsin (Sigma) and reacted for 30 min followed by heating to 90° C. to inactivate the pepsin.
Preparation of N,N'-diacetyl-chitobiose solution (Chitosan II):

A 5% N,N'-diacetyl-chitobiose solution in the above acetate buffer (pH 4.5) was then prepared by placing 5 gram of N,N'-diacetyl-chitobiose (Sigma) in a 150 mL glass beaker and adding 80 mL buffer pH 4.5. The solution was heated to 80° C., where the N,N'-diacetyl-chitobiose dissolves. The solution is cooled and stored at ambient temperature.

Example 2

In Vitro Glycosylation of Monoglyceride by Glycosyltranferase Using the Carbohydrate Solutions of Example 1 as Substrates $C_{10}$ based monoglyceride (glycerol monodecanoate, CAS No. 26402-22-2) is tested as acceptor substrate for transglycosidase reaction in a buffer based in vitro system.
Preparation:
Monodecanoate solution: 20% monodecanoate in acetate buffer (pH 6.0)

80 g of buffer pH 6.0 was placed in a 150 mL glass beaker and heated to 40-44° C. and 20 g of melted glycerol monodecanoate (Danisco A/S) added. The monodecanoate was dispersed in the water using an Ultra Turax for 20 sec. 10 gram of the monoglyceride dispersion is placed in 12×20 mL wheaton glass and treated according to Table 2.

TABLE 2

Treatment scheme

| Carbohydrate solution | Amount |
|---|---|
| Chitosan I | 1: 3 × 4 mL |
| Chitosan II | 2: 3 × 4 mL |

In Table 2, the transglycosidase enzyme used was a β-glucosidase from *Trichoderma reesei*, commercially available as Accellerase BG (3500 U/ml). 3500 U of this enzyme were used.

The glasses were placed in a heating block with magnetic stirring and temperature control and heated to 45° C. Each glass was added the first portion of carbohydrate solution and the reactions were initiated by addition of 100 U of the Accellerase BG (lot 16011709444) enzyme solution and incubated while stirring at 45° C. After 18 and 26 hours an additional portions of carbohydrate solutions were added to the reaction glasses to ensure that the equilibrium in the reaction mixture favour glycolipid formation. After 48 hours the reaction glasses were heat treated for 2 min in 90° C. water bath to inactivate the enzyme. Cooled to 25° C. and 1.5 mL samples were taken from each reaction glass. The samples were lyophilised to dryness. 2 mg of each sample were suspended in 100 μl chloroform/methanol/water/formic acid (50/50/10/0.5). 200 μl $H_2O$ was added and the sample mixture was shaken vigorously and the two liquid phases were separated by centrifugation. The upper phase ($H_2O$/methanol) was analysed by Liquid Chromatography-mass spectrometry (LC-MS) for the potential target products, using reversed-phase high-performance liquid chromatography coupled on-line with electrospray ionisation mass spectrometry in positive mode (HPLC/ESP-MS). The column was a C18 column and the gradient was based on water/acetone. Sodium acetate was added for adduct formation in positive mode. Formation of the target aminoglycosyl and N-acylaminoglycosyl monoglycerides (Compounds 1 and 2) shown below, as well as monogalactosyl monoglyceride (Reference Compound 1) was confirmed by MS/MS spectral analysis (see FIGS. 1 to 4).

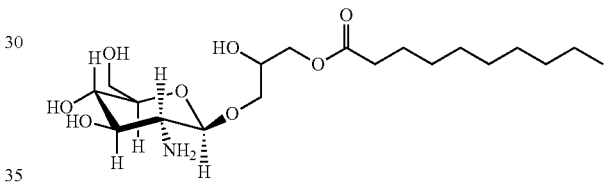

Compound 1: 3-O-(2-amino-2-deoxy-β-D-glucopyranosyl)-1-n-decanoylglycerol MW: 407.50 gram/mole

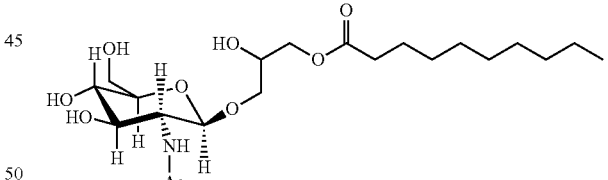

Compound 2: 3-O-(2-(acetylamino)-2-deoxy-β-D-glucopyranosyl)-1-n-decanoylglycerol MW=449.54 dram/mole

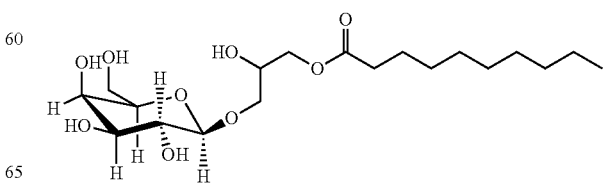

Reference Compound 1

1-O-(D-galactopyranosyl)-3-n-decanoylglycerol

TABLE 3

| Component identification by HPLC/MS | | | |
|---|---|---|---|
| Carbohydrate | Compound 1 | Compound 2 | Reference Compound 1 |
| Chitosan II | 0.251 | 2.177 | 0.020 |
| Chitosan I | 2.017 | 0.432 | 0.028 |

Examples 3 and 4

Chemical syntheses of
3-O-glucosaminyl-1-n-octadecanoylglycerol

Example 3:
Compound 3 was made according to Scheme 4 below.

In Scheme 4, "Bn" is benzyl.

Intermediate 1

2-acetamido-3,4,6-tri-O-acetyl-2-deoxy-α-D-glucopyranosyl chloride

This compound was prepared from N-acetyl-D-glucosamine according to literature procedures, for example as described in "Best Synthetic Methods: Carbohydrates", Elsevier Science Ltd. 2003, pp 69-80.

Intermediate 2

1-O-(2-acetamido-3,4,6-tri-O-acetyl-2-deoxy-α-D-glucopyranosyl)-2-O-benzyl-glycerol The compound of Intermediate 1 (8 g) was weighed into a 3-necked 500 ml round-bottomed flask fitted with a magnetic stirrer, condenser with drying tube and a thermometer. The compound was dissolved in $CH_2Cl_2$ (250 mL) and molecular

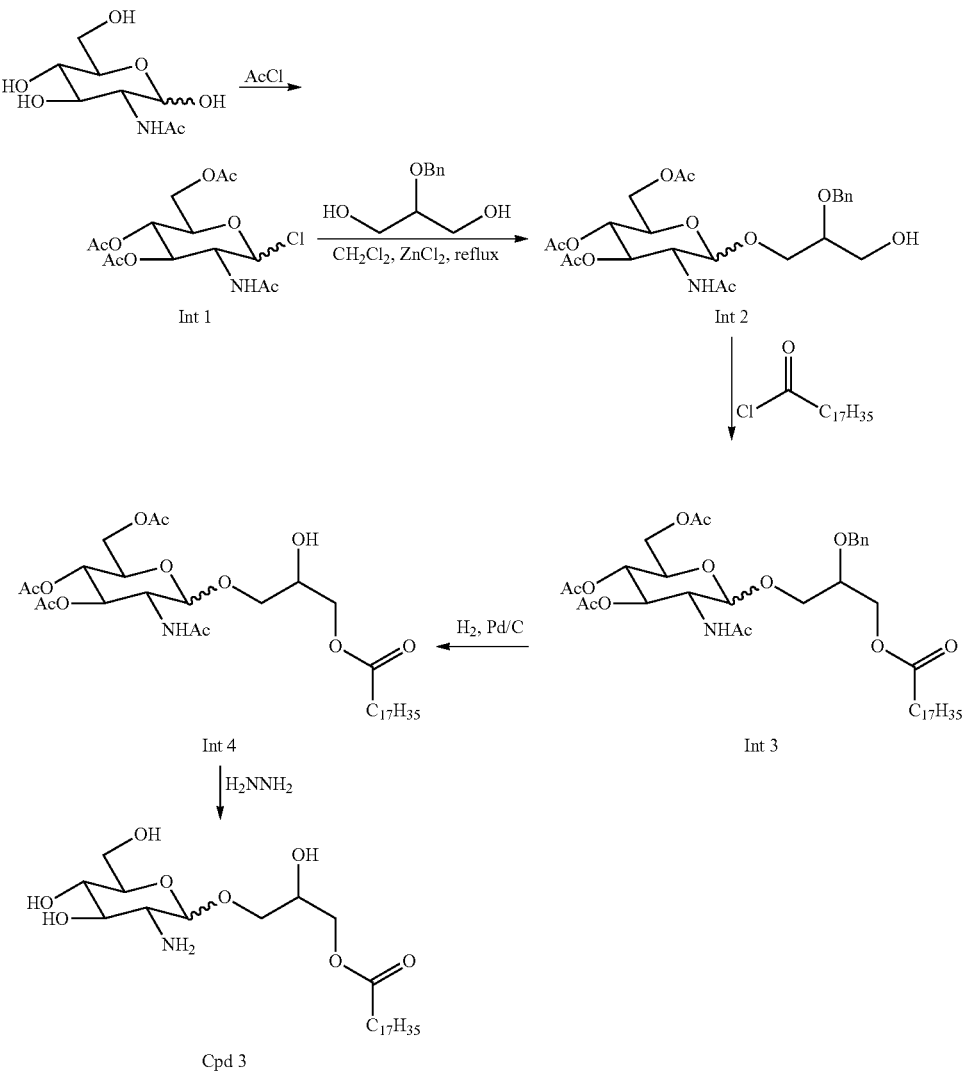

Scheme 4 sieves (4 Å, 2 g), 2-O-benzyl-glycerol (4.8 g) and ZnCl$_2$ (1.8 g) were added. The solution was refluxed overnight and cooled to room temperature. The reaction mixture wad washed with NaHCO$_3$ (Sat. aq., 2×200 mL) and water (200 mL). The organic phase was dried with Na$_2$SO$_4$, filtered and evaporated. The product was purified by column chromatography. The structure of Intermediate 2 was confirmed by $^1$H-NMR, $^{13}$C-NMR and infusion-electrospray-MS in positive mode (see FIGS. 8-15).

Intermediate 3

1-O-2-acetamido-3,46-tri-O-acetyl-2-deoxy-α-D-glucopyranosyl)-2-O-benzyl-3-n-octadecanoylglycerol The compound of Intermediate 2 (0.5 g) was dissolved in 10 mL dry CHCl$_3$ and added 60 mg pyridine and cooled to 0° C. 0.21 g of n-octadecanoyl chloride was dissolved in 10 mL dry CHCl$_3$ and added dropwise to the reaction during 1 hour maintaining the temperature at 0°. The reaction is continued at room temperature for 24 hours. 3 mL water was added to the reaction mixture and separated. The organic phase was washed with NaHCO$_3$ (Sat. aq., 2×3 mL) and water (3×2 mL). The organic phase was dried with MgSO$_4$, filtered and evaporated.

Figure 16:
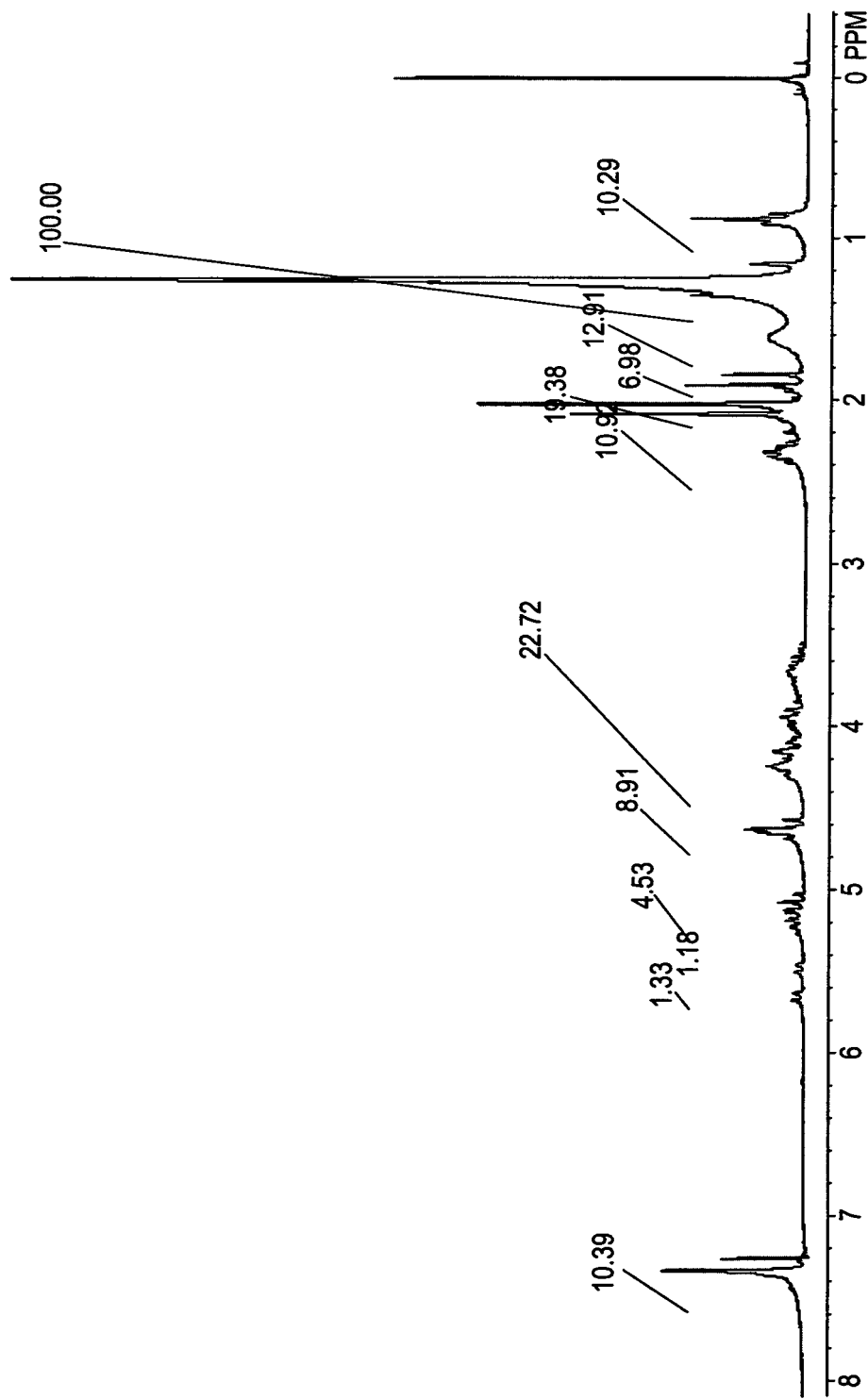
FIG. 16 is a $^1$H NMR spectrum of Intermediate 3.
Figure 17:
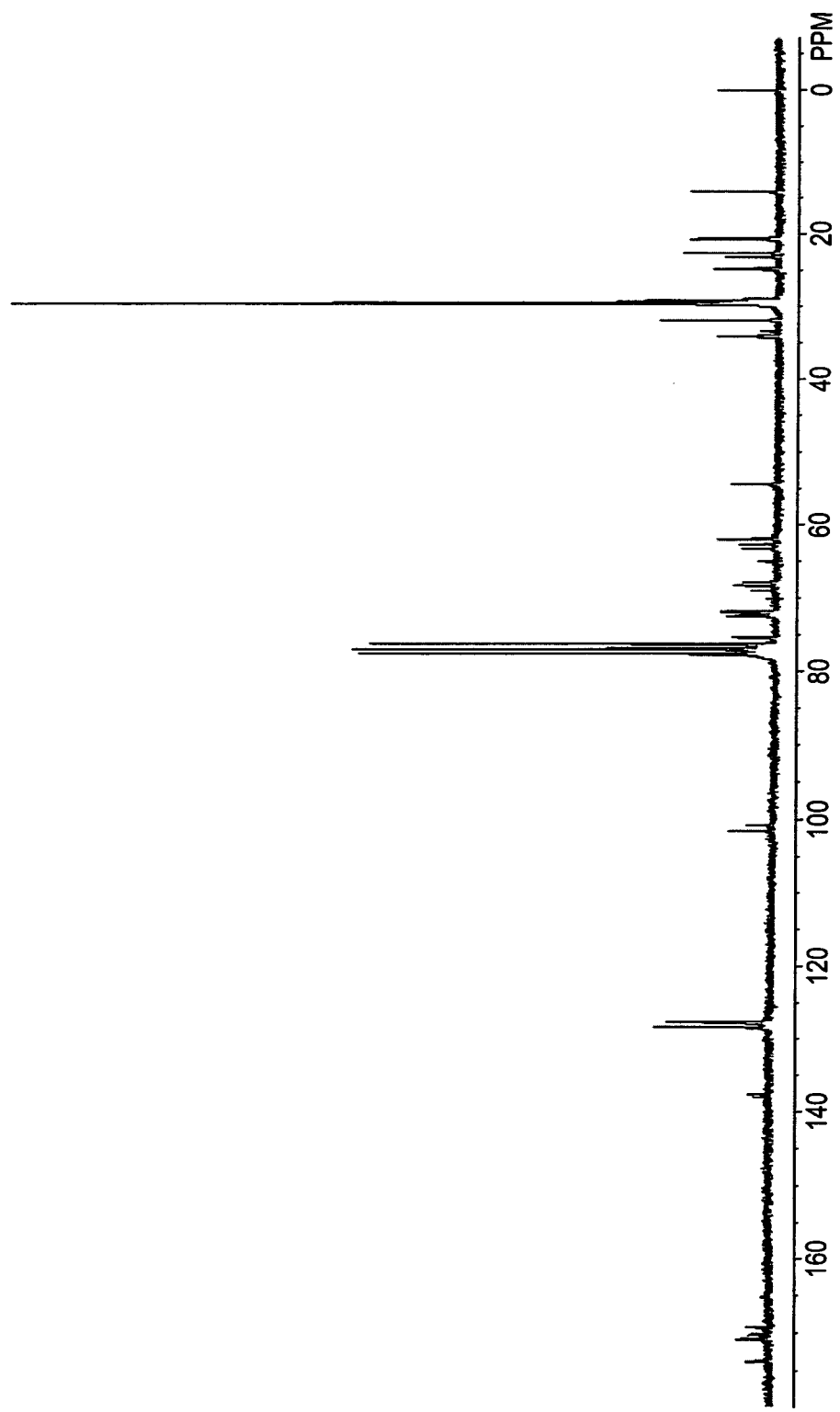
FIG. 17 is a $^{13}$C NMR spectrum of Intermediate 3.
Figure 18:
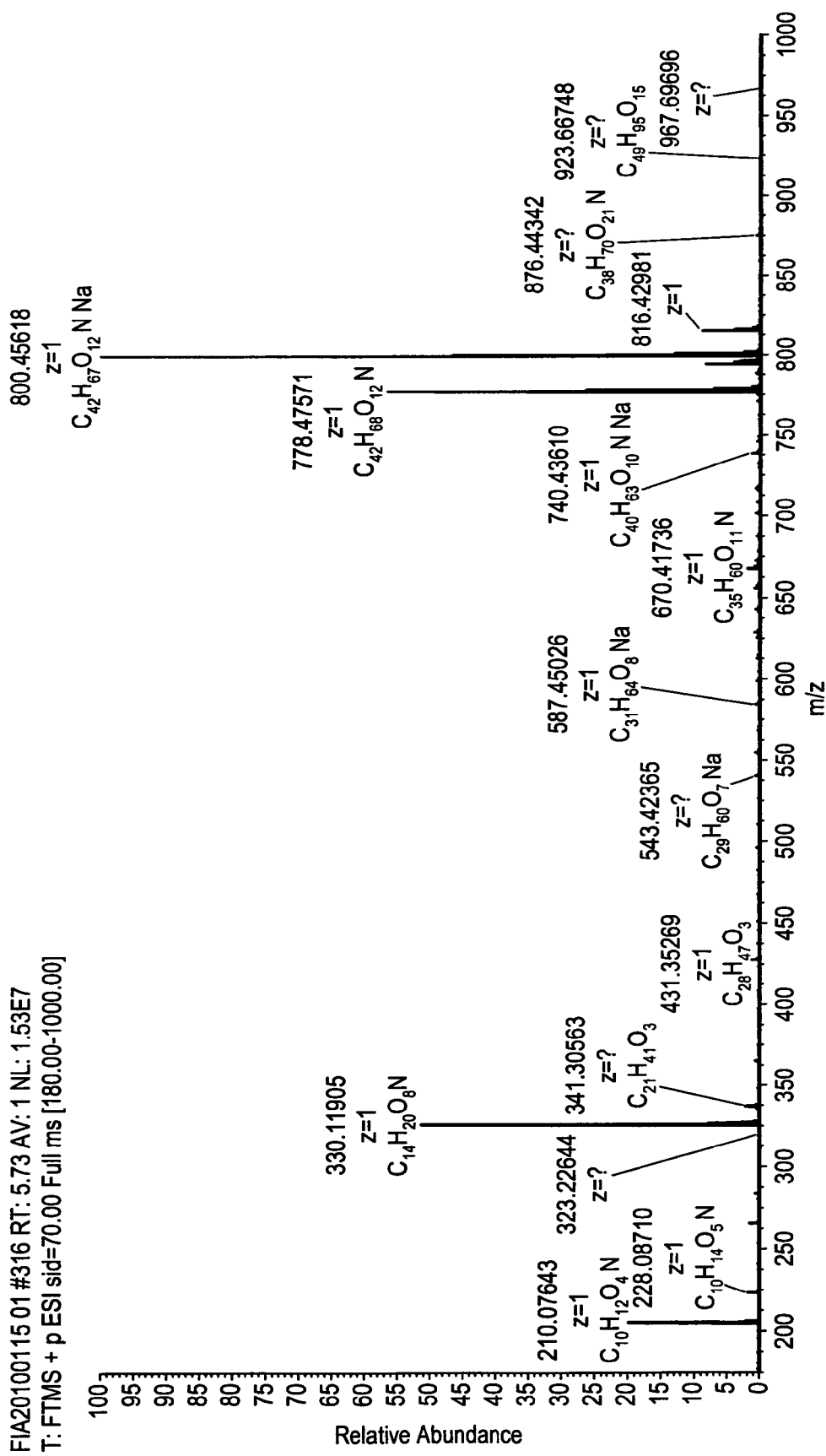
FIG. 18 is an MS spectrum of Intermediate 3.
Figure 19:
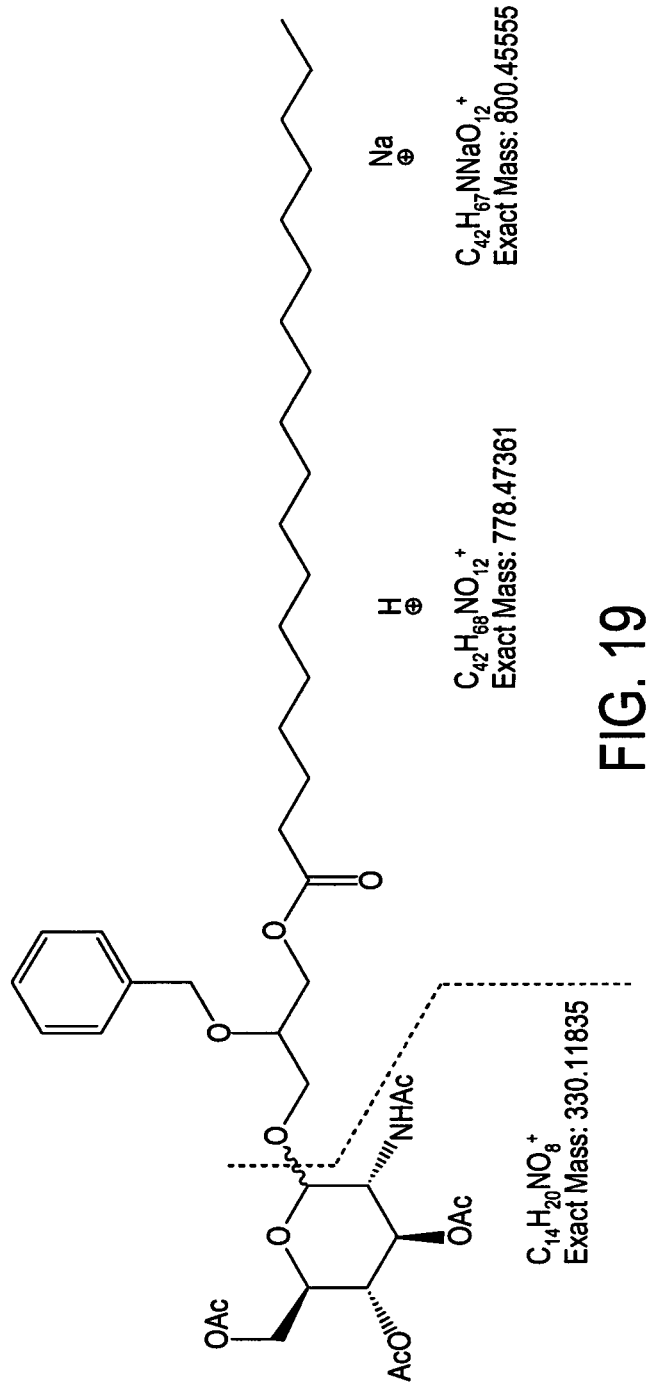
FIG. 19 assigns the fragments to the MS$^2$-spectrum of FIG. 18.

The structure of Intermediate 3 was confirmed by $^1$H-NMR, $^{13}$C-NMR and infusion-electrospray-MS in positive mode (see FIG. 16-18).

Intermediate 4

1-O-(2-acetamido-3,4,6-tri-O-acetyl-2-deoxy-α-D-glucopyranosyl)-3-n-octadecanoylglycerol The benzyl protecting group in the compound of Intermediate 3 can be removed by hydrogenation following a standard procedure described in *Eur. J. Org. Chem.*, 2006, 4, 978-985.

Compound 3

1-O-(2-amino-2-deoxy-α-D-glucopyranosyl)-3-n-octadecanoylglycerol

It is expected that the removal of the acetyl protecting groups on the sugar moiety of Intermediate 4 can be achieved by hydrazinolysis, according to the procedure described in *J. Agric. Food Chem.* 2008, 56, 6691-6700.

Example 4:

An alternative synthesis of Compound 3 is shown in Scheme 5 below.

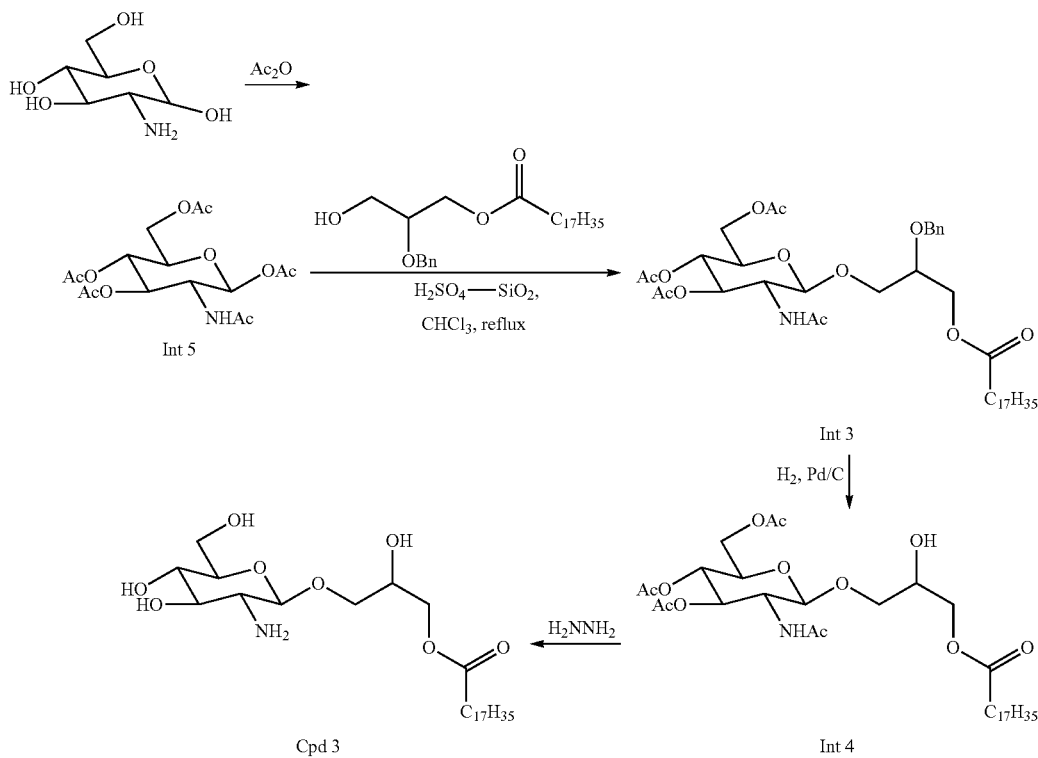

In Scheme 5, "Bn" is benzyl.

Intermediate 5

2-acetamido-1,3,4,6-tetra-O-acetyl-2-deoxy-α-D-glucopyranose

This compound was prepared from D-glucosamine hydrochloride according to literature procedures, for example as described in "Best Synthetic Methods: Carbohydrates", Elsevier Science Ltd. 2003, pp 69-80.

Intermediate 3

1-O-(2-acetamido-3,4,6-tri-O-acetyl-2-deoxy-α-D-glucopyranosyl)-2-O-benzyl-3-n-octadecanoylglycerol $H_2SO_4$-silica was prepared by adding conc. $H_2SO_4$ (1 mL) to a slurry of silica gel (10 g) in dry $Et_2O$ (50 mL) and the slurry was shaken for 5 min. The solvent was evaporated under reduced pressure resulting in free flowing $H_2SO_4$-silica which was dried at 110° C. overnight.

The compound of Intermediate 5,2-benzyl-1-n-octadecanoylglycerol and $H_2SO_4$-silica were dissolved in dry $CHCl_3$ and the reaction mixture was heated to reflux. After approx. 4 hours the reaction mixture was cooled to room temperature and filtered through Celite®. The product was purified by column chromatography. The structure of Intermediate 3 was confirmed by $^1$H-NMR, $^{13}$C-NMR and infusion-electrospray-MS in positive mode (see FIGS. 16-18).

Intermediate 4

1-O-(2-acetamido-3,4,6-tri-O-acetyl-2-deoxy-α-D-glucopyranosyl)-3-n-octadecanoylglycerol and Compound 3

1-O-(2-amino-2-deoxy-α-D-glucopyranosyl)-3-n-octadecanoylglycerol

Deprotection is expected to be accomplished as described above for Example 3.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in chemistry, biochemistry and biotechnology or related fields are intended to be within the scope of the following claims.

Aspects of the invention are defined in the following numbered paragraphs.

1. A compound of formula (I):

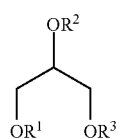

(I)

wherein:
a first group selected from $R^1$, $R^2$ and $R^3$ is an amino- or N-acylamino monosaccharide moiety, the acyl group having 1 to 6 carbon atoms, or an oligosaccharide chain comprising 2 to 4 monosaccharide moieties, at least one of which is an amino- or N-acylamino monosaccharide moiety;
a second group selected from $R^1$, $R^2$ and $R^3$ is a saturated or unsaturated acyl group having 3 to 40 carbon atoms; and
a third group selected from $R^1$, $R^2$ and $R^3$ is hydrogen; with the exception of an O-β-D-glucopyranosyl-(1→4)-O-2-acylamido-2-deoxy-β-D-glucopyranosylmonoacylglycerol.

2. A compound according to paragraph 1, wherein:
a first group selected from $R^1$ and $R^3$ is an amino- or N-acylamino monosaccharide moiety, the acyl group having 1 to 6 carbon atoms, or an oligosaccharide chain comprising 2 to 4 monosaccharide moieties, at least one of which is an amino- or N-acylamino monosaccharide moiety;
a second group selected from $R^1$ and $R^3$ is a saturated or unsaturated acyl group having 3 to 40 carbon atoms; and
$R^2$ is hydrogen.

3. A compound according to paragraph 1 or paragraph 2, wherein the first group is an amino- or N-acylamino monosaccharide moiety, the acyl group having 1 to 6 carbon atoms.

4. A compound according to paragraph 3, wherein the first group is an amino- or N-acylamino hexose moiety, the acyl group having 2 to 4 carbon atoms.

5. A compound according to paragraph 4, wherein the amino or N-acylamino group is present at the 2-position of the hexose moiety.

6. A compound according to paragraph 5, wherein the first group is selected from glucosamine or N-acetylglucosamine.

7. A compound according to any one of paragraphs 1 to 6, wherein the second group is a saturated or unsaturated acyl group having 6 to 24 carbon atoms.

8. A compound according to paragraph 7, wherein the second group is a saturated or unsaturated acyl group having 8 to 18 carbon atoms.

9. A compound according to paragraph 8, wherein the second group is n-decanoyl, n-dodecanoyl, n-tetradecanoyl, n-hexadecanoyl, n-octadecanoyl, cis-octadec-9-enoyl (oleyl), cis,cis-9,12-octadecadienoyl (linoleyl) or cis,cis,cis-9,12,15-octadecatrienoyl (linolenyl).

10. A compound according to paragraph 1, selected from:
1-O-(2-amino-2-deoxy-β-D-glucopyranosyl)-3-n-decanoylglycerol;
1-O-(2-(acetylamine)-2-deoxy-β-D-glucopyranosyl)-3-n-decanoylglycerol; and
1-O-(2-amino-2-deoxy-β-D-glucopyranosyl)-3-n-octadecanoylglycerol.

11. A method of preparing a compound according to any one of paragraphs 1 to 10, comprising contacting a monoacylglycerol, the acyl moiety thereof being a saturated or unsaturated acyl group having 3 to 40 carbon atoms, or an activated derivative thereof, with a source of amino- or N-acylamino monosaccharide moiety, or an activated derivative thereof, and, if required, a source of unsubstituted monosaccharide moiety, or an activated derivative thereof, optionally in the presence of a suitable catalyst or activating agent.

12. A method according to paragraph 11, wherein the catalyst or activating agent is a transglycosidase enzyme.

13. A method according to paragraph 11 or paragraph 12, wherein the acyl moiety of the monoacylglycerol is a saturated or unsaturated acyl group having 6 to 24 carbon atoms.

14. A method according to paragraph 13, wherein the acyl moiety of the monoacylglycerol is a saturated or unsaturated acyl group having 8 to 18 carbon atoms.

15. A method according to paragraph 14, wherein the acyl moiety of the monoacylglycerol is n-decanoyl, n-dodecanoyl, n-tetradecanoyl, n-hexadecanoyl, n-octadecanoyl, cis-octadec-9-enoyl (oleyl), cis,cis-9,12-octadecadienoyl (linoleyl) or cis,cis,cis-9,12,15-octadecatrienoyl (linolenyl).

16. A method according to paragraph 15, wherein the monoacylglycerol is 1-n-decanoyl-glycerol or 1-n-octadecanoyl-glycerol.

17. A method according to any one of paragraphs 11 to 16, wherein the source of amino- or N-acylamino monosaccharide moiety is selected from chitosan, chitobiose, or an N-acyl derivative of any thereof, the acyl group having 1 to 6 carbon atoms or a mixture of any thereof.

18. A method according to paragraph 17, wherein the source of amino- or N-acylamino monosaccharide moiety is selected from chitosan or chitobiose, or an N-acetyl derivative of either thereof.

19. A method according to any one of paragraphs 11 to 17, wherein the transglycosidase enzyme is classified in Enzyme Classification (E.C.) 3.2.1.21 or 3.2.1.74.

20. A method according to any one of paragraphs 11 to 17, wherein the transglycosidase enzyme is an aminoglycosyltransferase enzyme.

21. A method according to any one of paragraphs 11 to 17, wherein the transglycosidase enzyme is a β-glucosidase enzyme.

22. A method according to any one of paragraphs 11 to 21, wherein the transglycosidase enzyme is of fungal origin or has at least 50%, preferably at least 55%, such as at least 60%, at least 65%, at least 70%, at least 75%, at least 80%, at least 85%, at least 90%, at least 95%, at least 96%, at least 97%, at least 98% or at least 99%, sequence identity with a transglycosidase enzyme of fungal origin.

23. A method according to any one of paragraphs 11 to 21, wherein the transglycosidase enzyme originates from a *Trichoderma* species or has at least 50%, preferably at least 55%, such as at least 60%, at least 65%, at least 70%, at least 75%, at least 80%, at least 85%, at least 90%, at least 95%, at least 96%, at least 97%, at least 98% or at least 99%, sequence identity with a transglycosidase enzyme originating from a *Trichoderma* species.

24. A method according to any one of paragraphs 11 to 21, wherein the transglycosidase enzyme is *Trichoderma reesei* (SEQ ID No 1) or has at least 50%, preferably at least 55%, such as at least 60%, at least 65%, at least 70%, at least 75%, at least 80%, at least 85%, at least 90%, at least 95%, at least 96%, at least 97%, at least 98% or at least 99%, sequence identity therewith.

25. A method for in situ generation of a compound as defined in any of paragraphs 1-10 in a composition, the composition comprising the following components:
    (i) a monoacylglycerol, the acyl moiety thereof being a saturated or unsaturated acyl group having 3 to 40 carbon atoms, or an activated derivative thereof;
    (ii) a source of amino- or N-acylamino monosaccharide moiety, or an activated derivative thereof;
    (iii) if required, a source of unsubstituted monosaccharide moiety, or an activated derivative thereof; and
    (iv) if required, a suitable catalyst or activating agent; the method comprising adding to the composition any of components (i) and (ii) that are not already present in the composition and, if required (iii) and/or (iv) that are not already present in the composition, and allowing the components to react.

26. A foodstuff or feedstuff comprising a compound as defined in any of paragraphs 1-10 or produced by a method as defined in any of claims 10-24.

27. A foodstuff or feedstuff according to paragraph 26, additionally comprising one or more enzymes.

28. A foodstuff or feedstuff according to paragraph 27, wherein the one or more enzymes are selected from a protease, an amylase, a glucoamylase, a maltogenic amylase, a non-maltogenic amylase, a lipase, a cutinase, a carbohydrase, a cellulase, a pectinase, a mannanase, an arabinase, a galactanase, a xylanase, an oxidase, a laccase, and/or a peroxidase, or any combination thereof.

29. A detergent composition comprising a compound as defined in any of paragraphs 1-10 or produced by a method as defined in any of paragraphs 10-24.

30. A detergent composition according to paragraph 27, additionally comprising one or more enzymes.

31. A detergent composition according to paragraph 28, wherein the one or more enzymes are selected from a protease, an amylase, a glucoamylase, a maltogenic amylase, a lipase, a cutinase, a carbohydrase, a cellulase, a pectinase, a mannanase, an arabinase, a galactanase, a xylanase, an oxidase, a laccase, and/or a peroxidase, or any combination thereof.

32. Use of a compound according to any one of paragraphs 1 to 10 as an emulsifier.

33. Use according to paragraph 32, wherein the compound is used in combination with one or more enzymes.

34. Use according to paragraph 33, wherein the one or more enzymes are selected from a protease, an amylase, a glucoamylase, a maltogenic amylase, a non-maltogenic amylase, a lipase, a cutinase, a carbohydrase, a cellulase, a pectinase, a mannanase, an arabinase, a galactanase, a xylanase, an oxidase, a laccase, and/or a peroxidase, or any combination thereof.

35. Use of a compound according to any one of paragraphs 1 to 10 as a surfactant.

36. Use according to paragraph 35, wherein the compound is used in combination with one or more enzymes.

37. Use according to paragraph 36, wherein the one or more enzymes are selected from a protease, an amylase, a glucoamylase, a maltogenic amylase, a non-maltogenic amylase, a lipase, a cutinase, a carbohydrase, a cellulase, a pectinase, a mannanase, an arabinase, a galactanase, a xylanase, an oxidase, a laccase, and/or a peroxidase, or any combination thereof.

38. Use of a compound according to any one of paragraphs 1 to 10 as an antimicrobial agent.

39. Use according to paragraph 38, wherein the compound is used in combination with one or more enzymes.

40. Use according to paragraph 39, wherein the one or more enzymes are selected from a protease, an amylase, a glucoamylase, a maltogenic amylase, a non-maltogenic amylase, a lipase, a cutinase, a carbohydrase, a cellulase, a pectinase, a mannanase, an arabinase, a galactanase, a xylanase, an oxidase, a laccase, and/or a peroxidase, or any combination thereof.

The invention claimed is:

1. A method of preparing a compound of formula (I):

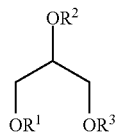

(I)

wherein:
a first group selected from $R^1$, $R^2$ and $R^3$ is an amino- or N-acylamino monosaccharide moiety, the acyl moiety of the N-acylamino group having 1 to 6 carbon atoms, or an oligosaccharide chain consisting of 2 to 4 monosaccharide moieties, at least one of which is an amino- or N-acylamino hexose moiety as defined above;

a second group selected from $R^1$, $R^2$ and $R^3$ is a alkanoyl and alkenoyl acyl group having 3 to 40 carbon atoms; and
a third group selected from $R^1$, $R^2$ and $R^3$ is hydrogen;
the method comprising contacting a monoacylglycerol, the acyl moiety thereof being a alkanoyl and alkenoyl acyl group having 3 to 40 carbon atoms, or an activated derivative thereof, with a source of amino- or N-acylamino monosaccharide moiety, or an activated derivative thereof, and, if required, a source of unsubstituted monosaccharide moiety, or an activated derivative thereof, optionally in the presence of a suitable catalyst or activating agent, wherein the catalyst or activating agent is a transglycosidase enzyme.

2. A method according to claim 1, wherein the source of amino- or N-acylamino monosaccharide moiety is selected from chitosan, chitobiose, or an N-acyl derivative of any thereof, the acyl moiety of the N-acylamino group having 1 to 6 carbon atoms or a mixture of any thereof.

3. A method according to claim 1, wherein the transglycosidase enzyme is a β-glucosidase enzyme.

4. A method according to claim 1, wherein the transglycosidase enzyme is *Trichoderma reesei* (SEQ ID No 1) or has at least 50%, at least 55%, at least 60%, at least 65%, at least 70%, at least 75%, at least 80%, at least 85%, at least 90%, at least 95%, at least 96%, at least 97%, at least 98% or at least 99%, sequence identity therewith.

5. A method for in situ generation of a compound of formula (I) as defined in claim 1 in a composition, the composition comprising the following components:
   (i) a monoacylglycerol, the acyl moiety thereof being a alkanoyl and alkenoyl acyl group having 3 to 40 carbon atoms, or an activated derivative thereof;
   (ii) a source of amino- or N-acylamino monosaccharide moiety, or an activated derivative thereof;
   (iii) a source of unsubstituted monosaccharide moiety, or an activated derivative thereof; and
   (iv) a suitable catalyst or activating agent, wherein the catalyst or activating agent is a transglycosidase enzyme;
the method comprising adding to the composition any of components (i) and (ii) that are not already present in the composition and, if required (iii) and/or (iv) that are not already present in the composition, and allowing the components to react.

* * * * *